(12) United States Patent
Leonardi et al.

(10) Patent No.: US 10,280,217 B2
(45) Date of Patent: May 7, 2019

(54) CELL CULTURE ADDITIVES AND THEIR USE FOR INCREASED BIOPROTEIN PRODUCTION FROM CELLS

(71) Applicant: American Air Liquide Inc., Houston, TX (US)

(72) Inventors: Jennifer Leonardi, Wilmington, DE (US); Flavio Schwarz, Wilmington, DE (US); Barbara Chiang, Wilmington, DE (US); Alice Tseng, Wilmington, DE (US)

(73) Assignee: American Air Liquide, Inc., Fremont, CA (US)

( * ) Notice: Subject to any disclaimer, the term of this patent is extended or adjusted under 35 U.S.C. 154(b) by 0 days.

(21) Appl. No.: 15/708,389

(22) Filed: Sep. 19, 2017

(65) Prior Publication Data
US 2019/0085060 A1 Mar. 21, 2019

(51) Int. Cl.
*C12N 5/07* (2010.01)
*C12N 1/38* (2006.01)
*C07K 16/18* (2006.01)
*C07K 16/06* (2006.01)

(52) U.S. Cl.
CPC ............ *C07K 16/18* (2013.01); *C07K 16/065* (2013.01); *C12N 1/38* (2013.01); *C12N 2500/02* (2013.01); *C12N 2511/00* (2013.01)

(58) Field of Classification Search
CPC ....... C07K 16/18; C12N 1/38; C12N 2500/02
See application file for complete search history.

(56) References Cited

U.S. PATENT DOCUMENTS

| | | |
|---|---|---|
| 2006/0051861 A1 | 3/2006 | Primiano |
| 2014/0273191 A1 | 9/2014 | Tipgunlakant et al. |
| 2015/0087024 A1 | 3/2015 | Pla et al. |

OTHER PUBLICATIONS

Du et al., Use of a small molecule cell cycle inhibitor to control cell growth and improve specific productivity and product quality of recombinant proteins in CHO cell cultures. Biotechnology & Bioengineering, vol. 112, No. 1 (Jan. 2015) pp. 141-155. (Year: 2015).*
Almo SC, Love JD. Better and faster: improvements and optimization for mammalian recombinant protein production. Current opinion in structural biology. 2014;26:39-43. doi:10.1016/j.sbi.2014.03.006.
Du, Zhimei, et al. "Use of a small molecule cell cycle inhibitor to control cell growth and improve specific productivity and product quality of recombinant proteins in CHO cell cultures." Biotechnology and bioengineering 112.1 (2015): 141-155.
Dhakshinamoorthy, S. and Porter, A.G., 2004. Nitric oxide-induced transcriptional up-regulation of protective genes by Nrf2 via the antioxidant response element counteracts apoptosis of neuroblastoma cells. Journal of Biological Chemistry, 279(19), pp. 20096-20107.
Loboda, A., Damulewicz, M., Pyza, E., Jozkowicz, A. and Dulak, J., 2016. Role of Nrf2/HO-1 system in development, oxidative stress response and diseases: an evolutionarily conserved mechanism. Cellular and Molecular Life Sciences, 73(17), pp. 3221-3247.
Luperchio, S., Tamir, S. and Tannenbaum, S.R., 1996. NO-induced oxidative stress and glutathione metabolism in rodent and human cells. Free Radical Biology and Medicine, 21(4), pp. 513-551.
Foresti, R. and Motterlini, R., 1999. The heme oxygenase pathway and its interaction with nitric oxide in the control of cellular homeostasis. Free radical research, 31(6), pp. 459-475.
Motterlini, R., Foresti, R., Intaglietta, M. and Winslow, R.M., 1996. NO-mediated activation of heme oxygenase: endogenous cytoprotection against oxidative stress to endothelium. American Journal of Physiology—Heart and Circulatory Physiology, 270(1), pp. H107-H114.
Bouton, C. and Demple, B., 2000. Nitric oxide-inducible expression of heme oxygenase-1 in human cells translation-independent stabilization of the mRNA and evidence for direct action of nitric oxide. Journal of Biological Chemistry, 275(42), pp. 32688-32693.
Marquis, J.C. and Demple, B., 1998. Complex genetic response of human cells to sublethal levels of pure nitric oxide. Cancer research, 58(15), pp. 3435-3440.
Brennan, M.S., Matos, M.F., Richter, K.E., Li, B. and Scannevin, R.H., 2017. The NRF2 transcriptional target, OSGIN1, contributes to monomethyl fumarate-mediated cytoprotection in human astrocytes. Scientific Reports, 7, p. srep42054.
Li, J., Billiar, T.R., Talanian, R.V. and Kim, Y.M., 1997. Nitric oxide reversibly inhibits seven members of the caspase family via S-nitrosylation. Biochemical and biophysical research communications, 240(2), pp. 419-424
Gevantman, L. H. "Solubility of selected gases in water." Nitric oxide (NO) 308.3.348 (2000): 10-4.
Zuckerbraun BS, Billiar TR, Otterbein SL, et al. Carbon Monoxide Protects against Liver Failure through Nitric Oxide-induced Heme Oxygenase 1. The Journal of Experimental Medicine. 2003;198(11):1707-1716. doi:10.1084/jem.20031003.
Wang, Jinling, et al. "Interaction of nitric oxide with human heme oxygenase-1." Journal of Biological Chemistry 278.4 (2003): 2341-2347.
Li F, Vijayasankaran N, Shen A (Yijuan), Kiss R, Amanullah A. Cell culture processes for monoclonal antibody production mAbs. 2010;2(5):466-477.
Butler, M., and A. Meneses-Acosta. "Recent advances in technology supporting biopharmaceutical production from mammalian cells." Applied microbiology and biotechnology 96.4 (2012): 885-894.

(Continued)

*Primary Examiner* — Kara D Johnson
(74) *Attorney, Agent, or Firm* — Allen E. White

(57) ABSTRACT

The invention relates to a method of increasing protein biomolecule production in which a) a cell that produces a heterologous protein biomolecule is cultured, and b) an Additive and/or a source of the Additive is added to the culture medium in an amount sufficient to (i) increase a total yield of the heterologous protein biomolecule secreted into the cell culture media and/or (ii) increase a specific cellular productivity of the heterologous protein biomolecule secreted into the cell culture media.

14 Claims, 31 Drawing Sheets

(56) References Cited

OTHER PUBLICATIONS

Clincke, Marie-Frangoise, et al. "Very high density of Chinese hamster ovary cells in perfusion by alternating tangential flow or tangential flow filtration in WAVE bioreactor™—part II: Applications for antibody production and cryopreservation." Biotechnology progress 29.3 (2013): 768-777.

Varley J, Birch J. Reactor design for large scale suspension animal cell culture. Cytotechnology. 1999;29(3):177-205. doi:10.1023/A:1008008021481.

Marks, David M. "Equipment design considerations for large scale cell culture." Cytotechnology 42.1 (2003): 21-33.

Ryter, Stefan W., and Augustine MK Choi. "Targeting heme oxygenase-1 and carbon monoxide for therapeutic modulation of inflammation." Translational Research 167.1 (2016): 7-34, pp. 13-14.

Keoni, C. L., & Brown, T. L. (2015). Inhibition of Apoptosis and Efficacy of Pan Caspase Inhibitor, Q-VD-OPh, in Models of Human Disease. Journal of Cell Death, 8, 1-7. http://doi.org/10.4137/JCD.S23844.

Mannick, J.B., Hausladen, A., Liu, L., Hess, D.T., Zeng, M., Miao, Q.X., Kane, L.S., Gow, A.J. and Stamler, J.S., 1999. Fas-induced caspase denitrosylation. Science, 284(5414), pp. 651-654.

Gegg, M. E., Beltran, B., Salas-Pino, S., Bolanos, J. P., Clark, J. B., Moncada, S. and Heales, S. J. R. (2003), Differential effect of nitric oxide on glutathione metabolism and mitochondrial function in astrocytes and neurones: implications for neuroprotection/neurodegeneration?. Journal of Neurochemistry, 86: 228-237. doi:10.1046/j.1471-4159.2003.01821.x.

Wright, Marcienne M., et al. "Fatty acid transduction of nitric oxide signaling: nitrolinoleic acid potently activates endothelial heme oxygenase 1 expression." Proceedings of the National Academy of Sciences of the United States of America 103.11 (2006): 4299-4304.

Origassa, Clarice Silvia Taemi, and Niels Olsen Saraiva Câmara. "Cytoprotective role of heme oxygenase-1 and heme degradation derived end products in liver injury." World journal of hepatology 5.10 (2013): 541.

Shields, R.L., Lai, J., Keck, R., O'Connell, L.Y., Hong, K., Meng, Y.G., Weikert, S.H. and Presta, L.G., 2002. Lack of fucose on human IgG1 N-linked oligosaccharide improves binding to human FcγRIII and antibody-dependent cellular toxicity. Journal of Biological Chemistry, 277(30), pp. 26733-26740.

Herter, S., Birk, M.C., Klein, C., Gerdes, C., Umana, P. and Bacac, M., 2014. Glycoengineering of therapeutic antibodies enhances monocyte/macrophage-mediated phagocytosis and cytotoxicity. The Journal of Immunology, 192(5), pp. 2252-2260.

International Search Report and Written Opinion for corresponding PCT/US2018/051712, dated Nov. 26, 2018.

* cited by examiner

Viable cell density (VCD) profiles of 5%, 2.5%, and 1% CO as compared to control conditions Viable cell densities of CHO-HBS cells exposed to nitrate.

FIG. 10 Titers of CHO-HBS bioreactor cultures exposed to nitrate.

NaNO$_2$ supplementation strategy mimics nitrite accumulation in media sparged with 300 ppm NO.

FIG. 12 Cellular growth in media supplemented with NaNO₂

Viable cell densities (left) and titers (right) from one experiment treating CHO cells with $NO_2$ (n=1 for $NO_2$ conditions, n=2 for controls).

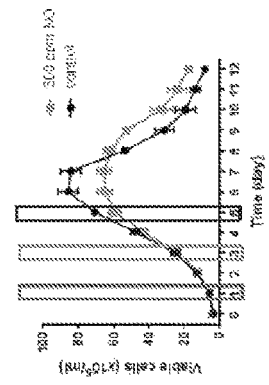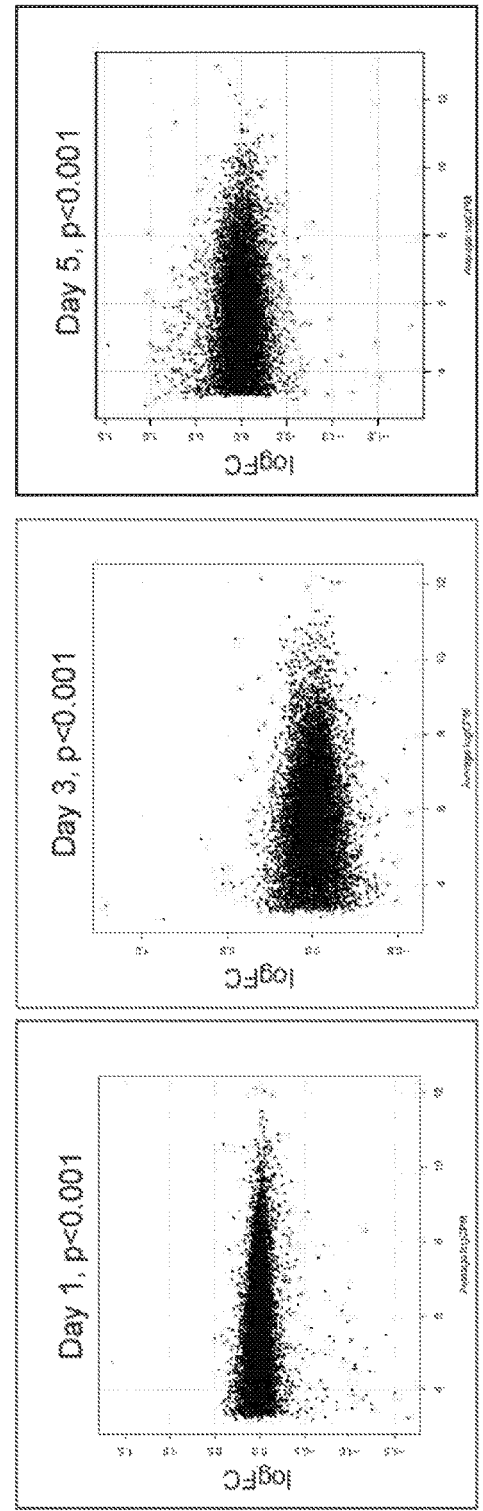
FIG. 16

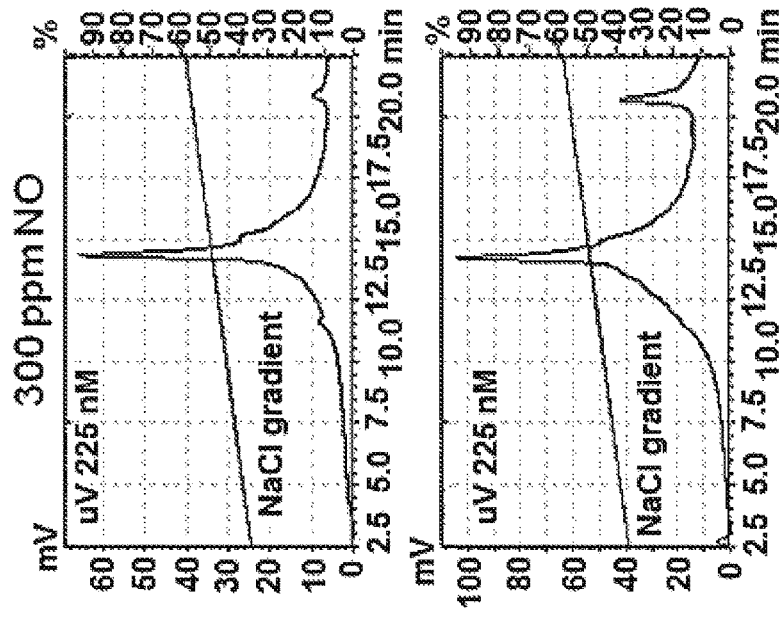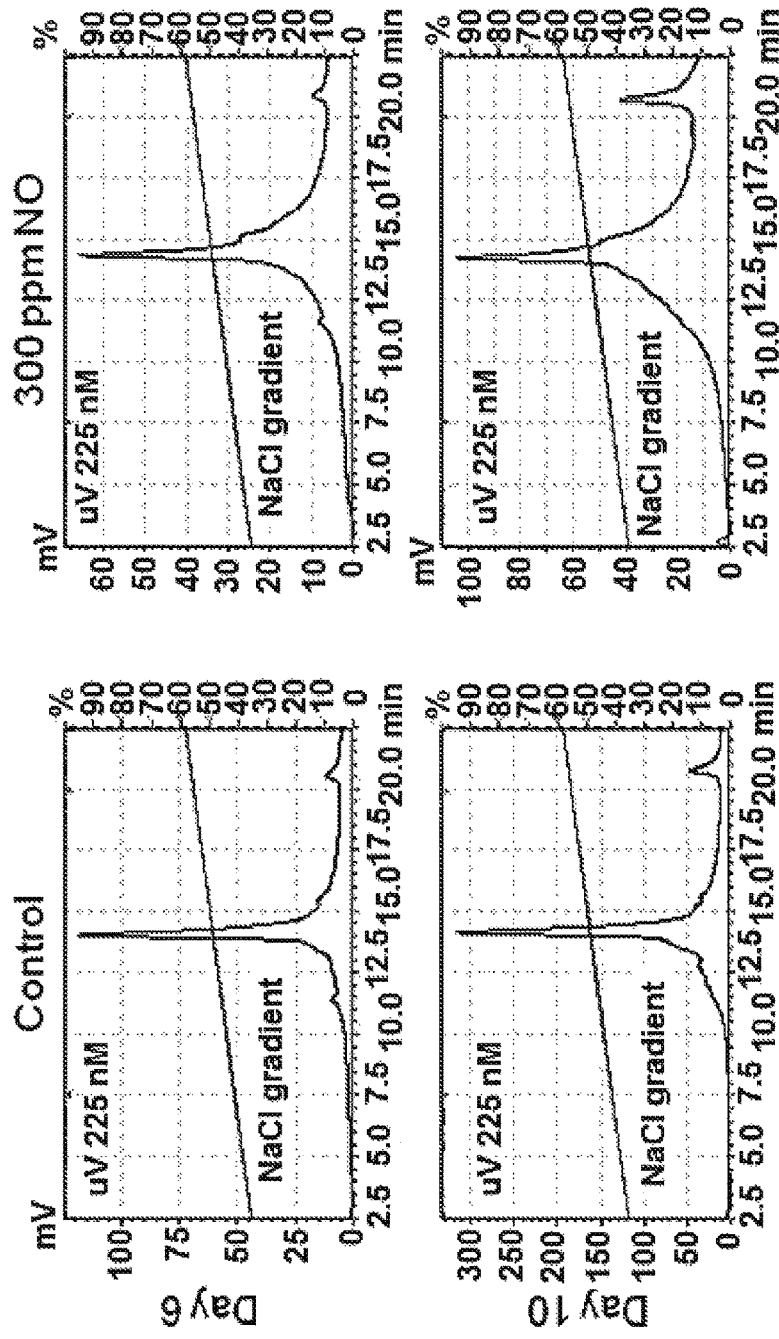
FIG. 30A  FIG. 30B  FIG. 30C  FIG. 30D

CELL CULTURE ADDITIVES AND THEIR USE FOR INCREASED BIOPROTEIN PRODUCTION FROM CELLS

TECHNICAL FIELD

The invention relates as its primary focus on enhancing cellular productivity and cell culture yield of protein containing biomolecules, in particular protein biopharmaceuticals such as monoclonal antibodies and small bioactive peptides produced by mammalian cells in cultures.

BACKGROUND ART

Recombinant human insulin became the first authorized biologic in 1982. Junod, Suzanne White. "Celebrating a milestone: FDA's approval of first genetically-engineered product." Update (2007): 43-44. The biologics industry has expanded dramatically since then with the addition of numerous new biologics, providing much needed therapeutic options for numerous diseases from hemophilia to cancer. In 2015, the U.S. FDA approved thirteen new biologics, nine of which were classified as "first-in-class" therapeutics. FDA Center for Drug Evaluation and Research, "Novel Drugs 2015 Summary", January 2016. <http://www.fda.gov/downloads/Drugs/DevelopmentApprovalProcess/DrugInnovation/UCM481709.pdf>.

The great promise of biologics as therapeutics faces numerous pragmatic challenges, not the least of which is the cost and complexity of production. The regulatory framework is also necessarily different than traditional small molecule pharmaceuticals:

"Because, in many cases, there is limited ability to identify the identity of the clinically active component(s) of a complex biological product, such products are often defined by their manufacturing processes. Changes in the manufacturing process, equipment or facilities could result in changes in the biological product itself and sometimes require additional clinical studies to demonstrate the product's safety, identity, purity and potency. Traditional drug products usually consist of pure chemical substances that are easily analyzed after manufacture. Since there is a significant difference in how biological products are made, the production is monitored by the agency from the early stages to make sure the final product turns out as expected."

U.S. FDA, Frequently Asked Questions About Therapeutic Biological Products, <http://www.fda.gov/Drugs/DevelopmentApprovalProcess/HowDrugsareDevelope dandApproved/ApprovalApplications/TherapeuticBiologicApplications/ucm113522.htm>.

Production and supply of biologics is therefore a key practical bottleneck in the flow of biologics to patients in need. Prices for biologics are correspondingly high relative to traditional small molecule chemical drugs. As a result, cost benefit analysis of biologics becomes critical in making decisions regarding access. See, e.g., Joensuu, Jaana T., et al. "The cost-effectiveness of biologics for the treatment of rheumatoid arthritis: a systematic review." PloS one 10.3 (2015): e0119683; Huoponen, Saara, and Marja Blom. "A Systematic Review of the Cost-Effectiveness of Biologics for the Treatment of Inflammatory Bowel Diseases." PloS one 10.12 (2015): e0145087.

In an effort to incentivize additional supply and lower costs, The U.S. federal government enacted the Biologics Price Competition and Innovation Act of 2009 as part of the Patient Protection and Affordable Care Act of 2010. This new law established the legal pathway and mandate for "biosimilars" i.e. generic biologics to secure market authorization. Ahmed, Isiah, Ben Kaspar, and Uma Sharma. "Biosimilars: impact of biologic product life cycle and European experience on the regulatory trajectory in the United States." Clinical therapeutics 34.2 (2012): 400-419. The European Medicines Agency has been at the global forefront of biosimilars regulation with the first biosimilar approvals. Ibid.

One means of improving supply and reducing cost would be improved productivity through cost effective measures to increase product yield from existing biologics manufacturing. Ideally this would be accomplished with minimal capital expense. And of course, the resultant product would have to survive a rigorous regulatory review and evaluation analogous to proposed biosimilars or "major" production process changes under FDA or other Medicines agencies' regulations (e.g. EMA).

Due to the intense commercial and healthcare pressures on biologics production and cost, the state of the art for biopharmaceutical production involves extensive, multifaceted optimization and manipulation of many parameters in creating and culturing cells for protein biomolecule production. Almo S C, Love J D. Better and faster: improvements and optimization for mammalian recombinant protein production. Current opinion in structural biology. 2014; 26:39-43. doi:10.1016/j.sbi.2014.03.006; Mammalian Cell Cultures for Biologics Manufacturing (2014) Advances in Biochemical Engineering/Biotechnology 139 (Zhou, W. and Kantardjieff, A. eds).

Many cell culture process manipulations are routinely used. Abu-Absi, Susan, et al. "Cell culture process operations for recombinant protein production." *Mammalian cell cultures for biologics manufacturing*. Springer Berlin Heidelberg, 2013. 35-68. For example, culture parameters, chemical agents and genetic engineering approaches have all been applied to cause cell cycle inhibition to increase specific cellular productivity to boost protein biomolecule yields. Du, Zhimei, et al. "Use of a small molecule cell cycle inhibitor to control cell growth and improve specific productivity and product quality of recombinant proteins in CHO cell cultures." Biotechnology and bioengineering 112.1 (2015): 141-155.

Despite the extensive and ongoing efforts to improve protein biomolecule production, there remains intense commercial pressure and medical need to find new ways for further improvement.

SUMMARY OF INVENTION

The invention may be understood in relation to the following non-limiting, exemplary embodiments:

In a first embodiment, the invention may be described in part by the following numbered sentences:

Sentence 1. A method of increasing protein biomolecule production comprising the steps of:

a) culturing a cell that produces a protein biomolecule, b) supplying an Additive, preferably Nitric Oxide, and/or a source of the Additive to the culture medium in an amount sufficient to (i) increase a total yield of the protein biomolecule secreted into the cell culture media and/or (ii) increase a specific cellular productivity of the protein biomolecule secreted into the cell culture media, c) wherein the increase of step b) is measured relative to:
culturing under a prior set of conditions established for a regulatory approval for producing the protein biomolecule and/or
culturing under substantially the same conditions except for supplying the Additive and/or a source of the Additive.

Sentence 2. The method of sentence 1, wherein (a) the Additive is Nitric Oxide and/or a chemical source of Nitric Oxide, (b) the cell is a eukaryotic cell, and (c) the protein biomolecule is a heterologous protein biomolecule.

Sentence 3. The method of sentence 1 and/or 2, wherein the eukaryotic cell is a CHO cell and the heterologous protein biomolecule is a monoclonal antibody.

Sentence 4. The method of sentence 1, 2, and/or 3, wherein the Nitric Oxide is gaseous and is substituted for a portion of a volume of another gas being fed into the bioreactor.

Sentence 5. The method of sentence 4, wherein the other gas being fed into the bioreactor includes Oxygen gas, Nitrogen gas and/or or Carbon Dioxide gas.

Sentence 6. The method of sentence 1, 2, 3, 4, and/or 5, wherein the Nitric Oxide and/or the chemical source of Nitric Oxide are added in an amount sufficient to increase a total yield of the monoclonal antibody secreted into the cell culture media.

Sentence 7. The method of sentence 1, 2, 3, 4, 5, and/or 6, wherein the Nitric Oxide and/or the chemical source of Nitric Oxide are added in an amount sufficient to increase a specific cellular productivity of the monoclonal antibody secreted into the cell culture media.

Sentence 8. The method of sentence 1, 2, 3, 4, 5, 6, and/or 7, wherein the Nitric Oxide soluble in the cell culture medium is at a concentration of 0.1-10 nanomolar.

Sentence 9. The method of sentence 8, wherein the Nitric Oxide is supplied to the cell culture medium as a sparged gas at a concentration of 200-400 ppm Nitric Oxide in the sparged gas.

Sentence 10. The method of sentence 1, 2, 3, 4, 5, 6, 7, 8, and/or 9, wherein the eukaryotic cell is a CHO cell and the heterologous protein biomolecule is a monoclonal antibody.

Sentence 11. The method of sentence 1, wherein the Additive is Carbon Monoxide, (b) the cell is a eukaryotic cell, and (c) the protein biomolecule is a heterologous protein biomolecule.

Sentence 12. The method of sentence 11, wherein the eukaryotic cell is a CHO cell and the heterologous protein biomolecule is a peptide or glycopeptide biologic.

Sentence 13. The method of sentence 11 and/or 12, wherein the Carbon Monoxide is added in an amount sufficient to increase a specific cellular productivity of the monoclonal antibody secreted into the cell culture media.

Sentence 14. The method of sentence 13, further comprising the steps of supplying to the culture medium at least two additional Additives capable of inducing HO-1 activity and inhibiting caspase-3 activity in the cell.

Sentence 15. The method of sentence 14, wherein the Additive to induce HO-1 activity is selected from one or more of curcumin, caffeic acid phenethyl ester, resveratrol, quercetin, epigallocatechin gallate, carnosol, sulforaphane, and dimethyl fumarate.

Sentence 16. The method of sentence 14, wherein the Additive to inhibit caspase-3 activity is selected from one or more of quinolyl-valyl-O-methylaspartyl-[-2,6-difluorophenoxy]-methyl ketone, Boc-D-fmk and Z-VAD-fmk.

Sentence 17. The method of sentence 14, further comprising the step of supplying to the culture medium an Additive capable of increasing glutathione levels in the cell.

Sentence 18. The method of sentence 17, wherein the Additive capable of increasing glutathione levels in the cell is selected from one or more of Benzyl isothiocyanate, β-naphthoflavone, coumarin, α-angelicalactone, disulfiram, indole-3-carbinol and indole-3-acetonitrile sulforaphane and dimethyl fumarate.

In a second embodiment, the invention may be described in part by the following numbered sentences:

Sentence 19. A bioreactor comprising a source of Nitric Oxide gas or a source of a chemical capable of forming Nitric Oxide, wherein the bioreactor is configured for and adapted to provide the Nitric Oxide or chemical capable of forming Nitric Oxide to a cell culture medium within the bioreactor.

Sentence 20. The bioreactor of sentence 19, wherein the bioreactor is configured for and adapted to commercial scale production of a heterologous protein biomolecule of at least 1000 mg/L per a cell culture batch or per a single, substantially contiguous cell culture production run.

Sentence 21. The bioreactor of sentence 19 and/or 20, wherein the bioreactor further comprises:
a) a Nitric Oxide sensor configured to and adapted for measuring the Nitric Oxide levels in the cell culture medium in the bioreactor,
b) a Nitric Oxide gas injector and/or a chemical injector operably connected to a supply of a chemical source of Nitric Oxide, and
c) a computer with a communication link to the Nitric Oxide sensor and electronically connected to the injector(s) of b), the computer specifically programmed to receive the Nitric Oxide sensor reading and modulate the injector(s) to maintain the Nitric Oxide concentration in the cell culture medium within a pre-determined concentration range and/or set point.

Sentence 22. The bioreactor of sentence 21, wherein the pre-determined concentration range is 0.1-10 nanomolar of Nitric Oxide solubilized in the cell culture medium.

Sentence 23. A method of operating the bioreactor of sentence 19, 20, and/or 21, comprising the step of providing the Nitric Oxide gas, and/or a chemical capable of forming Nitric Oxide, to the cell culture medium within the bioreactor of sentence 19, 20, and/or 21.

In a third embodiment, the invention may be described in part by the following numbered sentences:

Sentence 24. A cell culture medium comprising
a) a eukaryotic cell line that is capable of secreting a heterologous protein biomolecule, and
b) an Additive capable of causing an increase in the amount of heterologous protein biomolecule secreted by the eukaryotic cell.

Sentence 25. The cell culture medium of sentence 24, wherein the Additive is selected from one or more of Nitric Oxide gas mixed with the cell culture medium, Nitric Oxide dissolved in the cell culture medium and Carbon Monoxide.

Sentence 26. The cell culture medium of sentence 24 and/or 25, wherein (a) the Additive is Nitric Oxide, (b) the eukaryotic cell line is a CHO cell line, and (c) the heterologous protein biomolecule is a monoclonal antibody.

Sentence 27. The method of sentence 24, 25, and/or 26, wherein the Nitric Oxide soluble in the cell culture medium is within a concentration range of 0.1-10 nanomolar of Nitric Oxide.

In a fourth embodiment, the invention may be described in part by the following numbered sentences:

Sentence 28. A method of screening for a cell line that secretes a heterologous protein biomolecule and which is responsive to an Additive to result in an increased amount of secreted protein biomolecule, the method comprising the steps of:
  a) establishing a cell culture of the cell line that secretes the heterologous protein biomolecule,
  b) adding the Additive to the cell culture,
  c) measuring an amount of the secreted heterologous protein biomolecule protein biomolecule, and
  d) comparing the amount measured in step c) with an amount of secreted heterologous protein biomolecule representing a control condition lacking the addition of the Additive.

Sentence 29. The method of sentence 28, wherein the Additive is selected from one or more of Nitric Oxide gas, a chemical capable of forming Nitric Oxide, and Carbon Monoxide.

Sentence 30. The method of sentence 28 and/or 29, wherein (a) the Additive is selected from one or more of Nitric Oxide gas and a chemical capable of forming Nitric Oxide, (b) the cell line is a CHO cell line, and (c) the heterologous protein biomolecule is a monoclonal antibody.

DISCLOSURE OF INVENTION

The invention relates to the use of a cell culture additive (or additives, generically referred to herein as an "Additive") that increases the net yield of a protein biomolecule being produced by the cells being cultured. In a preferred group of embodiments, the protein biomolecule retains the same function and specific activity levels such that the protein biomolecule produced with the Additive may be substituted for the predicate protein biomolecule in compliance with any applicable regulatory requirements for safety, effectiveness, bioequivalence, and so forth.

Additive

The "Additive" is a chemical or combination of chemicals supplied to a cell culture that produces a net increase in the yield of a biomolecule produced by the cells in the cell culture.

Theory of Additive's Mechanism of Action

Additives take part in diverse reactions in culture media, yielding reactive oxygen and nitrogen species that can inflict cellular damage and induce stress. Cells combat oxidative stress by activating an array of detoxifying enzymes and other protective mechanisms that support cell survival. The transcription factor Nrf2 (Nuclear factor erythroid related factor 2) is a key player in the activation of such an oxidative stress response (Dhakshinamoorthy, S. and Porter, A. G., 2004. Nitric oxide-induced transcriptional up-regulation of protective genes by Nrf2 via the antioxidant response element counteracts apoptosis of neuroblastoma cells. Journal of Biological Chemistry, 279(19), pp. 20096-20107; Loboda, A., Damulewicz, M., Pyza, E., Jozkowicz, A. and Dulak, J., 2016. Role of Nrf2/HO-1 system in development, oxidative stress response and diseases: an evolutionarily conserved mechanism. Cellular and Molecular Life Sciences, 73(17), pp. 3221-3247). Under basal conditions, Nrf2 has a short half-life regulated by Keap1 (Kelch-like ECH-associated protein 1). Thiol groups of cysteins within Keap1 act as sensors for electrophiles and oxidants. In the presence of reactive oxygen species, cysteine residues of Keap1 become oxidized, leading to a conformational change, which prevents Keap1 binding to Nrf2. As a consequence, free Nrf2 is stabilized and translocates to the nucleus, where it drives expression of genes involved in antioxidant response.

Many Nrf2 targets are associated with glutathione metabolism. In the cell, glutathione can quench reactive oxygen and nitrogen species by forming glutathione-reactive species adducts (Luperchio, S., Tamir, S. and Tannenbaum, S. R., 1996. NO-induced oxidative stress and glutathione metabolism in rodent and human cells. *Free Radical Biology and Medicine,* 21(4), pp. 513-519). Moreover, the glutathione S-transferase (GST) conjugates hydrophobic electrophiles and reactive oxygen species with glutathione. In line with this, increased intracellular glutathione has been shown to provide greater resistance for cells during oxidative stress. Nrf2 controls expression of the enzyme responsible for glutathione biosynthesis glutamate-cysteine ligase (GCL), a heterodimer comprising a large catalytic subunit (GCLc) and a small regulatory subunit (GCLm). Glutathione homeostasis in the cell is also regulated by other factors such as recycling and cellular export. For instance, aerobic respiration may result in an increase in hydrogen peroxide, which is metabolized by glutathione peroxidase by converting two GSH molecules to GSSG. GSH can be recycled by the action of glutathione reductase.

Nrf2 drives the expression of heme oxygenase-1 (HO-1), the rate-limiting enzyme in heme degradation to CO, iron and bilirubin (Foresti, R. and Motterlini, R., 1999. The heme oxygenase pathway and its interaction with nitric oxide in the control of cellular homeostasis. Free radical research, 31(6), pp. 459-475). As free heme can catalyze the production of free radicals, in homeostatic conditions, this pro-oxidant property is controlled by keeping the heme groups in proteins. However, under oxidative stress, proteins can release their heme groups. Cells respond by inducing the expression of HO-1, which breaks down heme and avoids cell death. Bilirubin can also act as a potent peroxyl radical scavenger (Motterlini, R., Foresti, R., Intaglietta, M. and Winslow, R. M., 1996. NO-mediated activation of heme oxygenase: endogenous cytoprotection against oxidative stress to endothelium. American Journal of Physiology-Heart and Circulatory Physiology, 270(1), pp. H107-H114). Free iron leads to induction of ferritin, a protective enzyme that sequesters iron and limits free iron from participation in the Fenton reaction. Other indirect effect could arise from low levels of carbon monoxide generated by HO-1 that inhibit proliferation. Whereas the dose/response curve depends on the cell type, low levels of Additives in the range of 1-30 nM/s are typically associated with HO-1 induction (Bouton, C. and Demple, B., 2000. Nitric oxide-inducible expression of heme oxygenase-1 in human cells translation-independent stabilization of the mRNA and evidence for direct action of nitric oxide. Journal of Biological Chemistry, 275(42), pp. 32688-32693; Marquis, J. C. and Demple, B., 1998. Complex genetic response of human cells to sublethal levels of pure nitric oxide. Cancer research, 58(15), pp. 3435-3440). Nrf2 may also induce expression of specific isoforms of the oxidative stress induced cell inhibitor Osgin1 (Brennan, M. S., Matos, M. F., Richter, K. E., Li, B. and Scannevin, R. H., 2017. The NRF2 transcriptional target, OSGIN1, contributes to monomethyl fumarate-mediated cytoprotection in human astrocytes. Scientific Reports, 7, p.srep42054).

The cytoprotective effects of Additives include a reduction of a form of cell death called 'programmed cell death' or 'apoptosis'. This type of cell death is typically started by proteases called caspases. All caspases contain a single cysteine at the enzyme catalytic site that is essential for activity. For caspase-3, the cysteine 163 is susceptible to redox modification and can be efficiently S-nitrosylated in the presence of nitric oxide (Brennan, M. S., Matos, M. F., Richter, K. E., Li, B. and Scannevin, R. H., 2017. The NRF2 transcriptional target, OSGIN1, contributes to monomethyl fumarate-mediated cytoprotection in human astrocytes. Scientific Reports, 7, p.srep42054). Suppression of caspase activity by Additives has been demonstrated using several purified human caspases and has been shown to account, at least in part, for the inhibition of apoptosis by Additives both in vivo and in vitro (Li, J., Billiar, T. R., Talanian, R. V. and Kim, Y. M., 1997. Nitric oxide reversibly inhibits seven members of the caspase family via S-nitrosylation. Biochemical and biophysical research communications, 240(2), pp. 419-424).

Altogether, low concentrations of Additives provide high cellular viability for an extended period of time, resulting in production boost of biomolecules. Per the below experiments, nitrite, nitrate, nitrogen dioxide or carbon monoxide show neutral or negative effects on overall biomolecules production yields, indicating that nitric oxide specifically increases biomolecules production despite a counterbalancing negative impact on cell culture densities. Incubation of cells with a chemical that provides controlled release of nitric oxide in the medium resulted in extended viability. Nitric oxide has been shown to cause oxidative damage to mitochondria that may or may not be counteracted by elevated glutathione via increased activity in enzymes that produce glutathione. This is a secondary effect of nitric oxide that is distinct from the HO-1 mechanism by which increased biomolecule production results. Nonetheless, it is obviously preferable that the cells used in the invention respond to nitric oxide in this manner for optimal increase in cell density, viability and protein biomolecule yield, if nitric oxide is the Additive used.

Examples of nitric oxide for use as an Additive include a) nitric oxide gas of an appropriate concentration in a nitrogen or other inert balance gas, b) nitric oxide gas generated continuously by one of several known devices (e.g., Pezone, Matthew J., et al. "Nitrogen dioxide reducing ascorbic acid technologies in the ventilator circuit leads to uniform NO concentration during inspiration." Nitric Oxide 58 (2016): 42-50.), and/or c) nitric oxide gas of an appropriate concentration with an appropriate concentration of carbon dioxide in an inert balance gas. In certain preferred embodiments, the Additive is nitric oxide provided as the molecule itself or a pro-molecule(s) that becomes or produces nitric oxide. Examples of pro-molecules for providing nitric oxide include:

DETA-NO (diethylenetriamine-nitric oxide adduct, CAS #146724-94-9), a NO donor that spontaneously dissociates in a pH-dependent, first-order process with a half-life of 20 hours at 37° C., pH 7.4 to liberate 2 moles of NO per mole of parent compound.

β-Gal-NO (CAS #357192-77-9), a NO donor which releases NO following activation by β-galactosidase with a half-life of six minutes at pH 5.6.

NOC-5 (CAS #146724-82-5), a NO donor that releases two equivalents of NO in solution under physiological conditions. The half-life of NOC-5 in PBS (pH 7.4) is 93 minutes at 22° C.

DEA-NO (CAS #372965-00-9), a NO donor that spontaneously dissociates in a pH-dependent, first-order process with a half-life of 2 minutes at 37° C., pH 7.4, to liberate 1.5 moles of NO per mole of parent compound DPTA-NO (CAS #146724-95-0), a NO donor that spontaneously dissociates in a pH-dependent, first-order process with a half-life of three hours at 37° C., pH 7.4 to liberate 2 moles of NO per mole of parent compound MAHMA NONOate (CAS #146724-86-9), a NO donor that spontaneously dissociates in a first-order process with a half-life of 1 minute at 37° C., pH 7.4 to liberate 2 moles of NO per mole of parent compound PAPA NONOate (CAS #146672-58-4), a NO donor that spontaneously dissociates in first-order process with a half-life of 15 minutes at 37° C., pH 7.4 to liberate 2 moles of NO per mole of parent compound Common Structural and/or Chemical Features of the Additives Nitric Oxide ("NO") and Carbon Monoxide ("CO") are both diatomic molecules with an oxygen atom bonded to a non-oxygen atom. Both are soluble in water to comparable levels. Gevantman, L. H. "Solubility of selected gases in water." Nitric oxide (NO) 308.3.348 (2000): 10-4. Both molecules influence Hemeoxygenase-1 mediated cellular functions. See, e.g., Zuckerbraun B S, Billiar T R, Otterbein S L, et al. Carbon Monoxide Protects against Liver Failure through Nitric Oxide-induced Heme Oxygenase 1. *The Journal of Experimental Medicine*. 2003; 198(11):1707-1716. doi:10.1084/jem.20031003; Wang, Jinling, et al. "Interaction of nitric oxide with human heme oxygenase-1." *Journal of Biological Chemistry* 278.4 (2003): 2341-2347 (Abstract: "NO and CO may complement each other as signaling molecules in some physiological situations.").

Cellular Responses to Additives and Distinguishing Characteristics of Cells Cultured with Additives Protein Biomolecules Protein Biomolecules are amino acid containing molecules that may also have a variety of other chemical constituents such as lipids, carbohydrates or phosphates. In general, the amino acid component is the predominant part of the overall molecular mass of the Protein Biomolecule. Protein Biomolecules may be naturally occurring molecules, modified version of natural molecules such as through genetic engineering to make selected changes to the translated amino acid sequence or antibody chimera, or wholly man made molecules based for example on protein crystallography guided peptide engineering approaches. The preferred Protein Biomolecules are those having medical uses which are generally peptides such as erythropoietin (EPOGEN™; PROCRIT™) or monoclonal antibodies such as Adalimumab (HUMIRA™).

Cells

The cultured cells that respond to the Additive to yield increased biomolecule production are eukaryotic cells, generally mammalian cells such as Chinese Hamster Ovary (CHO) cells, murine myeloma (NSO, Sp2/0) cells, and Human Embryonic Kidney Cells (HEK). These cells share the ability to add post translational modifications to complex proteins which are similar to those in humans and induce oxidative stress response.

Cell Culture

Cells for producing Protein Biomolecules are cultured in a suitable liquid medium in bioreactors. Li F, Vijayasankaran N, Shen A (Yijuan), Kiss R, Amanullah A. Cell culture processes for monoclonal antibody production. *mAbs.* 2010; 2(5):466-477; Wang, Dianliang, et al. "The bioreactor a powerful tool for large-scale culture of animal cells." *Current pharmaceutical biotechnology* 6.5 (2005): 397-403; Butler, M., and A. Meneses-Acosta. "Recent advances in technology supporting biopharmaceutical production from mammalian cells." *Applied microbiology and biotechnology* 96.4 (2012): 885-894. The most common format for large scale monoclonal antibody production is a bioreactor is a stainless steel stirred tank having temperature, pressure, agitation, pH and dissolved oxygen controls and sensor systems for pH, dissolved $CO_2$, etc. The most common medium/culturing format is fed-batch. Li F, Vijayasankaran N, Shen A (Yijuan), Kiss R, Amanullah A. Cell culture processes for monoclonal antibody production. *mAbs.* 2010; 2(5):466-477; Yang J-D, Lu C, Stasny B, Henley J, Guinto W, Gonzalez C, et al. Fed-batch bioreactor process scale-up from 3 L to 2,500 L scale for monoclonal antibody production from cell culture. *Biotechnol Bioeng.* 2007; 98:141-154.

Many other bioreactor and media-culturing formats are now available for large scale production of Protein Biomolecules such as WAVE™ bioreactors for perfusion cultures. Clincke, Marie-Françoise, et al. "Very high density of Chinese hamster ovary cells in perfusion by alternating tangential flow or tangential flow filtration in WAVE Bioreactor™—part II: Applications for antibody production and cryopreservation." *Biotechnology progress* 29.3 (2013): 768-777; Chotteau, Véronique, Ye Zhang, and Marie-Francoise Clincke. "Very High Cell Density in Perfusion of CHO Cells by ATF, TFF, Wave Bioreactor, and/or CellTank Technologies-Impact of Cell Density and Applications." *Continuous Processing in Pharmaceutical Manufacturing* (2014).

Use of Chemical Additives to Bioreactor Media

Bioreactors are designed to add a variety of media components as stock liquid concentrates. Generally, the bioreactors include a media feed system connected by a conduit to the bioreactor chamber. The media feed system draws additional media, or constituents thereof, from source containers and feeds these into the bioreactor generally under automated control. Most often, there is computer automation with programming to add various components to the bioreactor based on a schedule, sensor feedback loop, etc. pH, glucose levels, and other actively managed parameters are modulated by the addition of various media components and other chemicals into the bioreactor. These facets of bioreactor engineering are old and well established technology. Telling, R. C., and C. J. Stone. "A method of automatic pH control of a bicarbonate-CO2 buffer system for the submerged culture of hamster kidney cells." *Biotechnology and Bioengineering* 6.2 (1964): 147-158; Varley J, Birch J. Reactor design for large scale suspension animal cell culture. *Cytotechnology.* 1999; 29(3):177-205. doi:10.1023/A: 1008008021481; Marks, David M. "Equipment design considerations for large scale cell culture." *Cytotechnology* 42.1 (2003): 21-33.

BRIEF DESCRIPTION OF DRAWINGS

For a further understanding of the nature and objects for the present invention, reference should be made to the following detailed description, taken in conjunction with the accompanying drawings, in which like elements are given the same or analogous reference numbers and wherein:

FIG. 16 shows the differential expression readouts from RNAseq analysis of cells at three time points (days 1, 3 and 5) from 3 L cultures of CHO-HSB cells exposed to Nitric Oxide ("NO") gas supplied at 300 ppm on the cell culture sparging gas;

FIG. 30A shows ion exchange chromatography profiles of IgGs from control reactors at Day 6 at pH 5.8;

FIG. 30B shows ion exchange chromatography profiles of IgGs from control reactors at Day 10 at pH 5.8;

FIG. 30C shows ion exchange chromatography profiles of IgGs from reactors spared with 300 ppm NO at Day 6 at pH 5.8;

FIG. 30D shows ion exchange chromatography profiles of IgGs from reactors spared with 300 ppm NO at Day 10 at pH 5.8.

MODE(S) FOR CARRYING OUT THE INVENTION

Candidate Additives Tested

The following candidate gaseous and chemical additives were screened using a batch CHO cell process in a 3 L (2 L working volume) bioreactors. CHO-HBS cells were cultured in CDM4MAb media (HyClone Laboratories; Logan Utah; custom part containing base media cat# SH30801.02 supplemented with an additional 0.5 g/L poloxamer 188) in vented, plain-bottom Erlenmeyer flasks at 3-30×10$^5$ cells/mL. The cells were cultured for 14-16 days and then inoculated into 3 L semi-batch bioreactors at 3-4×10$^5$ cells/mL with 2 L working volumes. The bioreactor system monitored and controlled temperature, pH, % $CO_2$, %02, sparge rate, and aeration rate. The bioreactors maintained a sparge rate of 0.1 vvm, 40% DO, and a pH value of 7.10. The pH was controlled by addition of $CO_2$ or 1 N sodium bicarbonate solution. Additionally, 1 M glucose was added and adjusted daily to allow for a glucose consumption rate of 3 g/L/day. Each bioreactor was sampled daily (3-4 mL removed/day) for analysis. Gaseous additives were injected into the bioreactors using the following methods:

Inert Gas Injection (xenon): The bioreactor system controlled the flowrate and composition of oxygen, carbon dioxide, air, and nitrogen that was sparged into each bioreactor. The mixture composition was determined by the dissolved oxygen and pH levels in each reactor. House gas lines for these four gases were filtered and fed into the bioreactor mass flow control system. The effects of xenon were tested by replacing the nitrogen house gas feed with a cylinder containing xenon and replacing the air gas feed with a cylinder containing 21% oxygen and 79% xenon respectively. The system was calibrated for controlling the flowrate of the replacement gas by measuring the bioreactor mass flow controller flowrate for each gas at 12slph using a film flowmeter, then adjusting the gas correction factor for the bioreactor nitrogen or air mass flow controller until the flowrate on the film flowmeter and bioreactor system were the same. Therefore, xenon completely replaced nitrogen in the gas stream during the experiment, which resulted in sparging of 25-75% xenon into the bioreactors. This allowed the CHO cells to be cultured with the maximum quantity of inert gas.

Reactive Gas Injection (nitric oxide, carbon monoxide, or hydrogen): The bioreactor module controlled the composition and flow of oxygen, air, nitrogen, and carbon dioxide gases as described previously. Reactive gases including nitric oxide, carbon monoxide, or hydrogen were introduced into the gas stream through a tee line connection before the gas mixture entered the bioreactors. The reactive gas flowrate was controlled using a mass flow controller and the flowrate of the bioreactor controlled mixture was adjusted to maintain the total gas flowrate into each reactor at 12slph.

Xenon and Hydrogen (Gaseous)

Figure 2:
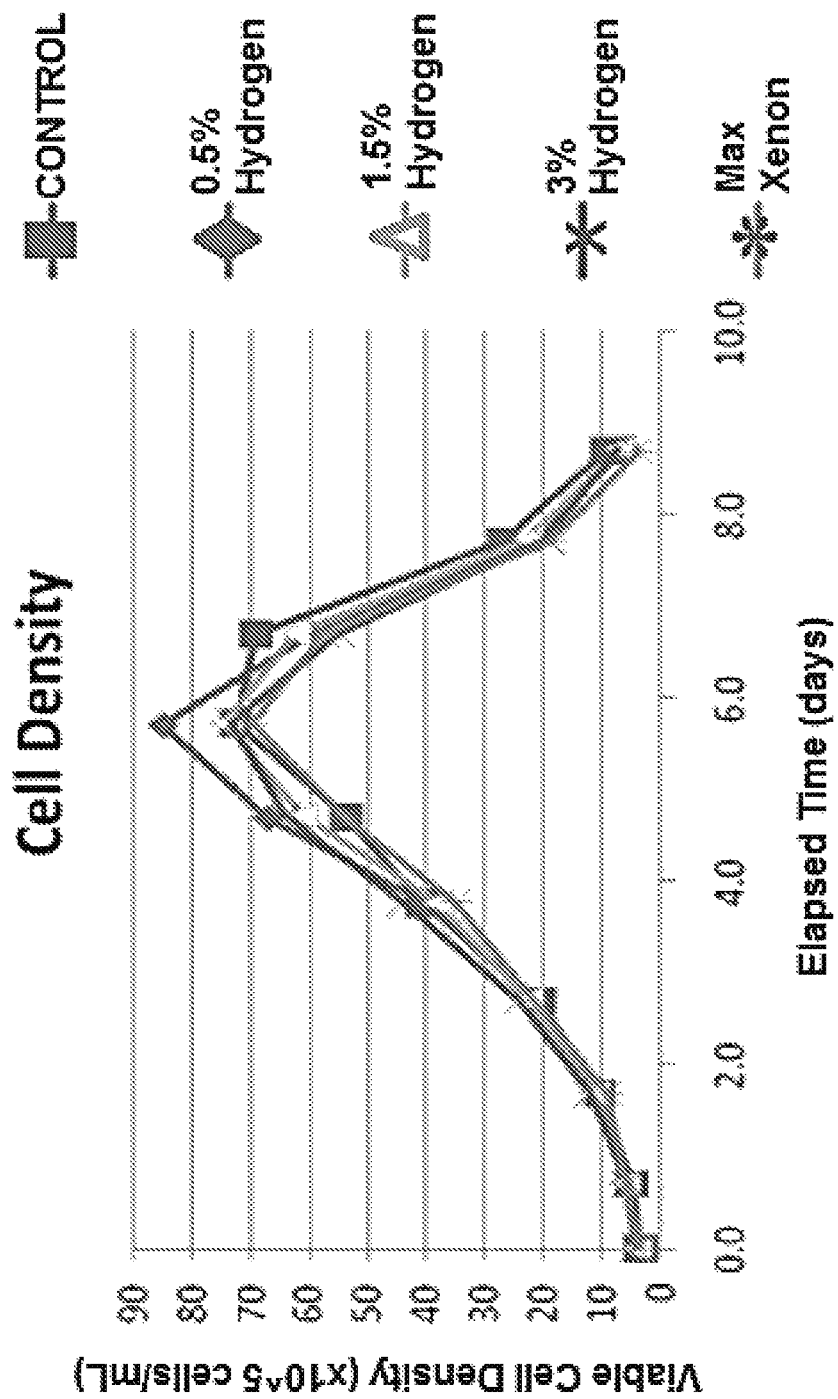
FIG. 2 shows the viable cell density curves for cultures of CHO-HBS cells exposed to Hydrogen gas or Xenon gas.
Figure 3:
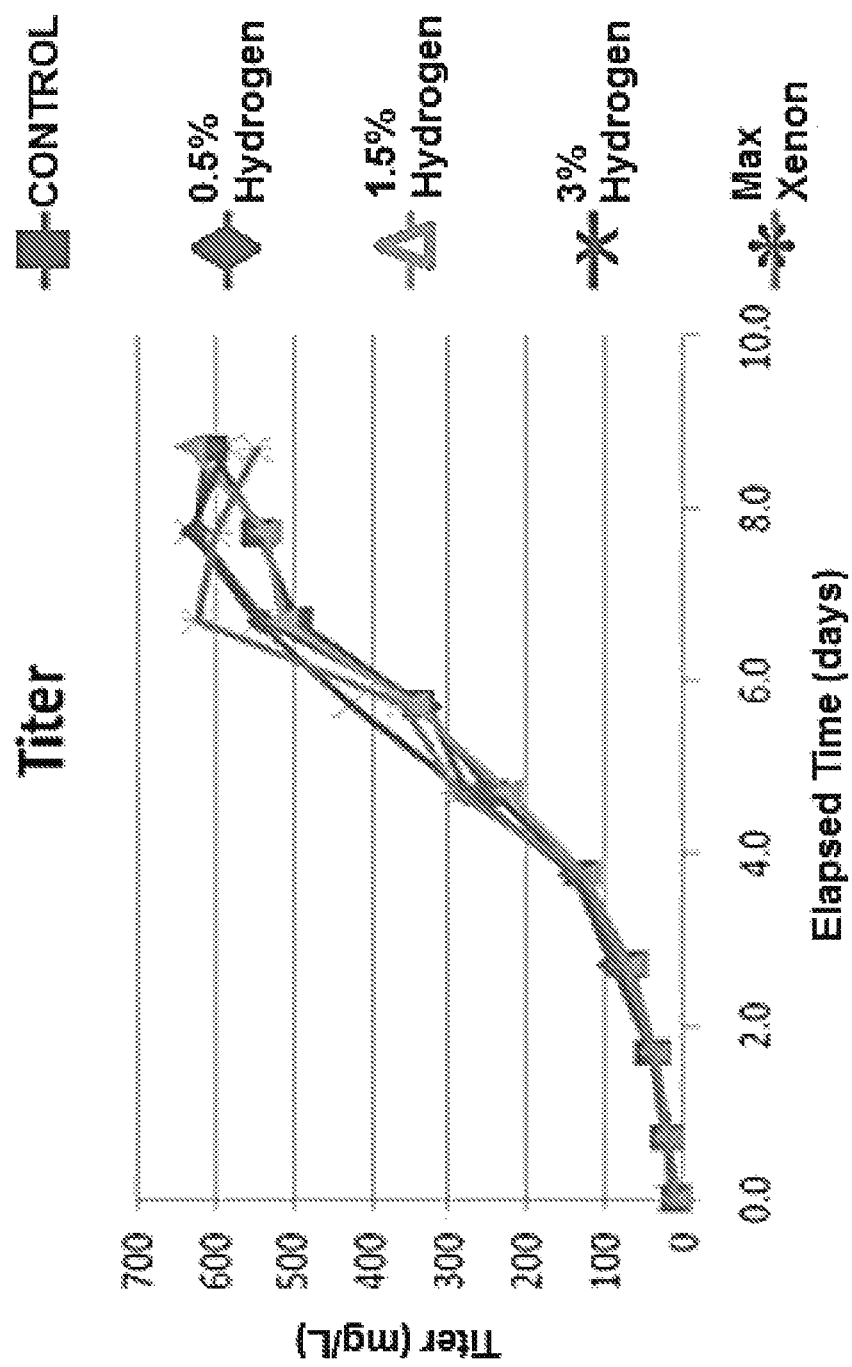
FIG. 3 shows the titer of monoclonal antibody for cultures of CHO-HBS cells exposed to Hydrogen gas or Xenon gas.

Exemplary results of cell culture sparging with Xenon and Hydrogen are shown in FIGS. 2 and 3, respectively. The two main parameters observed are viable cell density (VCD) and antibody titer, from which one derives cellular specific productivity (qP). These results are typical for gaseous Additives that do not have a significant impact on protein biomolecule production or cell growth. Other gaseous additives that did not significantly affect CHO cell cultures included Argon and Krypton.

Carbon Monoxide (Gaseous)

Figure 4:
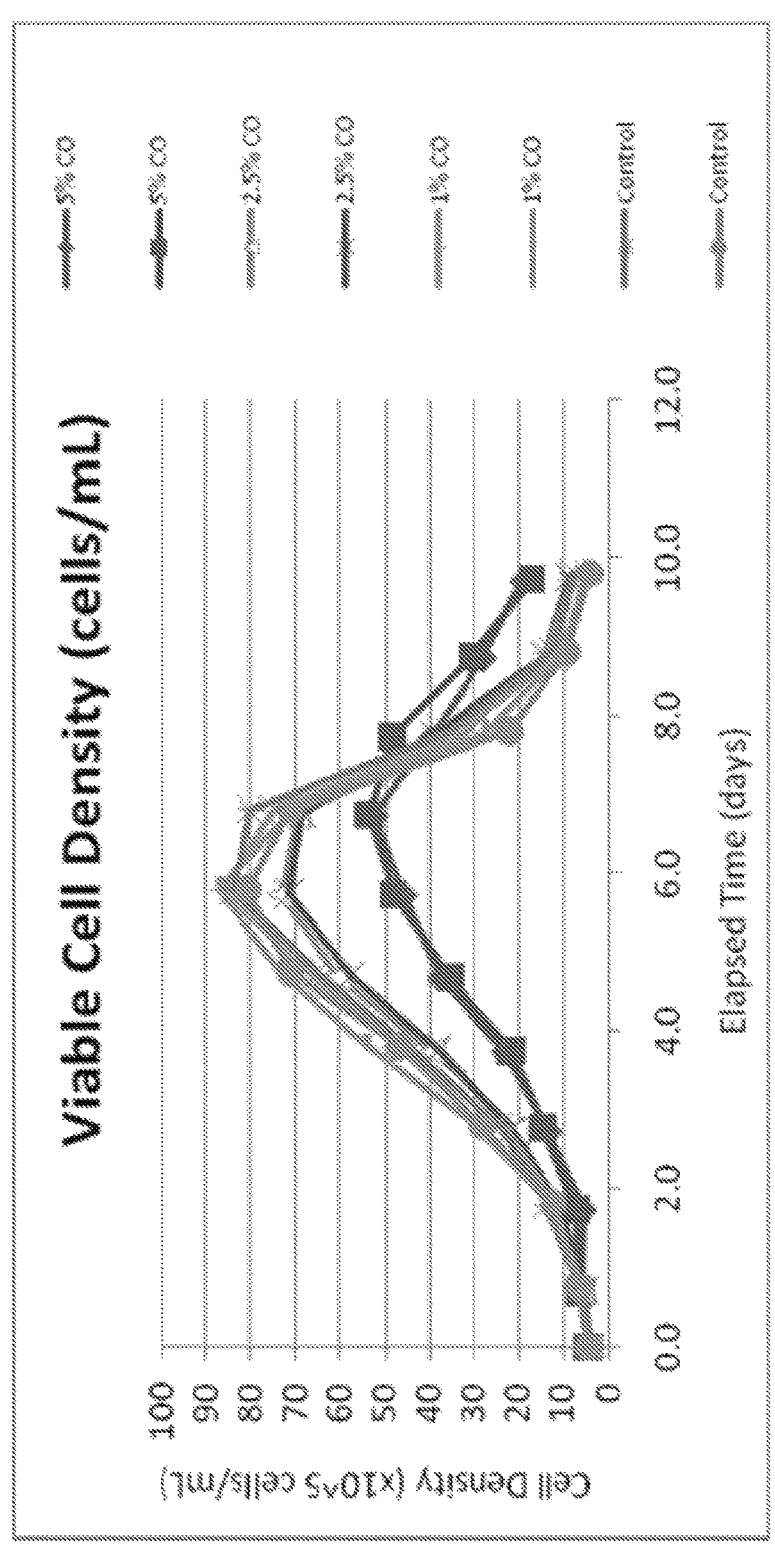
FIG. 4 shows viable cell density of batch 3 L cultures of CHO-HSB cells exposed to Carbon Monoxide ("CO") gas.

In contrast to Xenon, Argon, Krypton and Hydrogen, Carbon Monoxide showed a pronounced impact on cell growth (FIG. 4). Above a threshold amount between 2.5% and 5% Carbon Monoxide in the sparging gas, cell growth was affected. VCD is suppressed during the growth phase, but shows higher VCD at the end of the culturing period compared with the control. Despite the marked change in VCD over time, the final antibody titer was less impacted. The calculated qP was thus higher than control. But the net effect of VCD to qP produced an overall smaller yield in Batch cell cultures in bioreactors. Thus carbon monoxide is an Additive that functions to increase the amount of protein biomolecule produced by cells, but has the undesirable effect of suppressing cell growth to the point that overall yield from a culture is reduced. One means of improving on Carbon Monoxide's effect in cell culture bioreactors would be to limit the period of exposure to start later in the cell culture growth phase to balance the growth inhibition effect against the qP increase.

Figure 1:
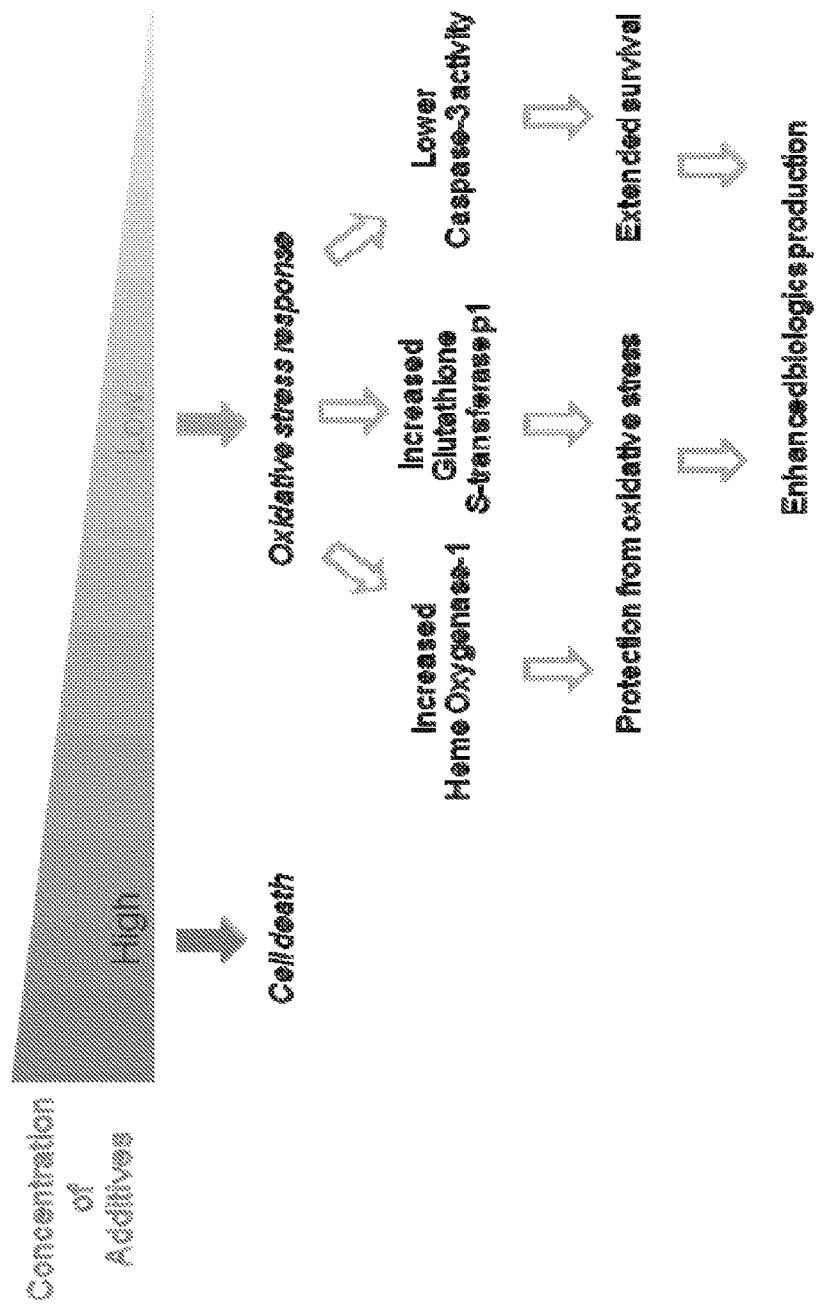
FIG. 1 illustrates the theoretical mechanism of action for the Additives described herein.

In contrast to Nitric Oxide ("NO"), discussed below, cells exposed to Carbon Monoxide ("CO") did not lead to an increase of enzymes involved in the oxidative stress response such as HO-1 (FIG. 1). This difference demonstrates why the preferred Additive is NO. While CO increases qP, the cytoprotective induction of HO-1 is lacking, resulting in a lower VCD that counteracts the positive effects of CO in terms of overall batch yields. Additional benefits of CO will be realized with the addition of other HO-1 inducing adjunct Additives. Many compounds are well known to induce HO-1. HO-1 inducing compounds are a known collection of classes of molecules from the state of the art scientific literature:

Natural and Synthetic HO-1-Inducing Compounds
A subclass of HO inducing agents includes electrophilic antioxidant compounds, many of which are plant-derived polyphenols found in the human diet. These compounds activate the Nrf2 system resulting in the enhanced expression of several Nrf2 target genes coding for detoxification-associated proteins (e.g., HO-1, glutathione S-transferase A2 and NADPH: quinone oxidoreductase).[247-248] Among the natural compounds that can induce HO-1 in model systems include the plant-derived compounds curcumin,[12-14] caffeic acid phenethyl ester,[13-14] resveratrol,[11] quercetin,[15-17] epigallocatechin gallate,[18-19] camosol,[248] sulforaphane[248] and others. The effectiveness of these dietary compounds at inducing HO-1 using in vitro model systems has led to a hypothesis that these or related compounds may be used as pharmaceuticals for human conditions such as cardiovascular disease.[249] A recent study has evaluated the effectiveness of high dose oral curcumin administration in humans.[250] This study concluded that oral curcumin was ineffective at inducing HO-1 in human peripheral blood mononuclear cells after administration, due to poor absorption.[250] Further studies are needed to identify safe and effective oral compounds that can induce HO-1 in humans.

In addition to dietary compounds, several pharmaceutical compounds have been identified that can activate Nrf2/Keap1 axis, including dimethyl fumarate (DMF) and related compounds.[248] Fumarates have been used in the treatment of psoriasis, while DMF has shown therapeutic effects in Phase III clinical trials for multiple sclerosis. An oral formulation of DMF (e.g., BG-12, Tecfidera) has been approved for clinical use in the treatment of multiple sclerosis in the USA, Canada, Europe and Australia.[251-252] The mechanism of action of DMF, or its downstream metabolite monomethyl fumarate, involves the direct modification of a critical cysteine thiol group of Keap1 (Cys151) resulting in Nrf2 stabilization.[253-254] DMF can act as a potent inducer of HO-1 in microglia cells and can confer anti-inflammatory effects in this cell type.[248] Application of DMF can confer neuroprotection, reduce macrophage inflammation, and increase IL-10 production in mouse models of chronic experimental autoimmune encephalomyelitis.[253,255] DMF also reduced intimal hyperplasia in a model of vascular injury, in an Nrf2-dependent mechanism involving upregulation of $p21^{Cip1}$.[256] The effects of Nrf2-inducing compounds such as DMF are not necessarily specific for HO-1, as Nrf2 regulates multiple effector enzymes. Further research may lead to the development of additional Nrf2-activating compounds for safe and effective activation of the antioxidant response in the context of human disease.

Ryter, Stefan W., and Augustine M K Choi. "Targeting heme oxygenase-1 and carbon monoxide for therapeutic modulation of inflammation." Translational Research 167.1 (2016): 7-34, pages 13-14. Cell lines may also be transformed with constitutive or inducible HO-1 transgenes to create a modified cell line with improved yields in response to CO as an Additive. Ibid, page 14.

Additional benefits of CO will also be realized with the addition of caspase-3 inhibiting adjunct Additives and intracellular glutathione inducing adjunct Additives. Many compounds are well known to inhibit caspase-3. Caspase-3 inhibiting compounds are a known collection of classes of molecules from the state of the art scientific literature. See, e.g., Ekert, P. G., J. Silke, and D. L. Vaux. "Caspase inhibitors." Cell Death & Differentiation 6.11 (1999); Keoni, C. L., & Brown, T. L. (2015). Inhibition of Apoptosis and Efficacy of Pan Caspase Inhibitor, Q-VD-OPh, in Models of Human Disease. Journal of Cell Death, 8, 1-7. http://doi.org/10.4137/JCD.S23844.

Nitric Oxide (Gaseous)

Figure 5:
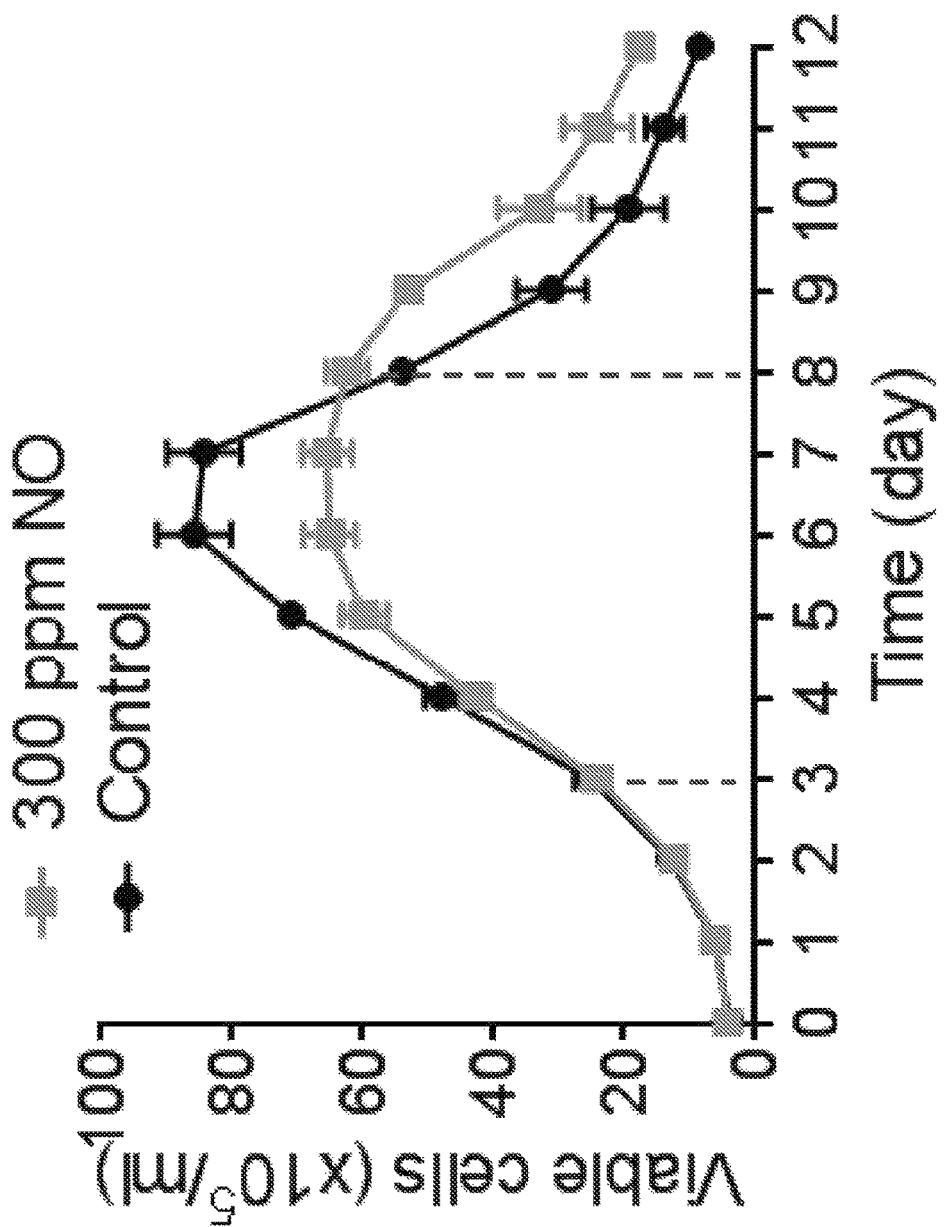
FIG. 5 shows viable cell density of batch 3 L cultures of CHO-HSB cells exposed to Nitric Oxide ("NO") gas supplied at 300 ppm on the cell culture sparging gas.
Figure 6:
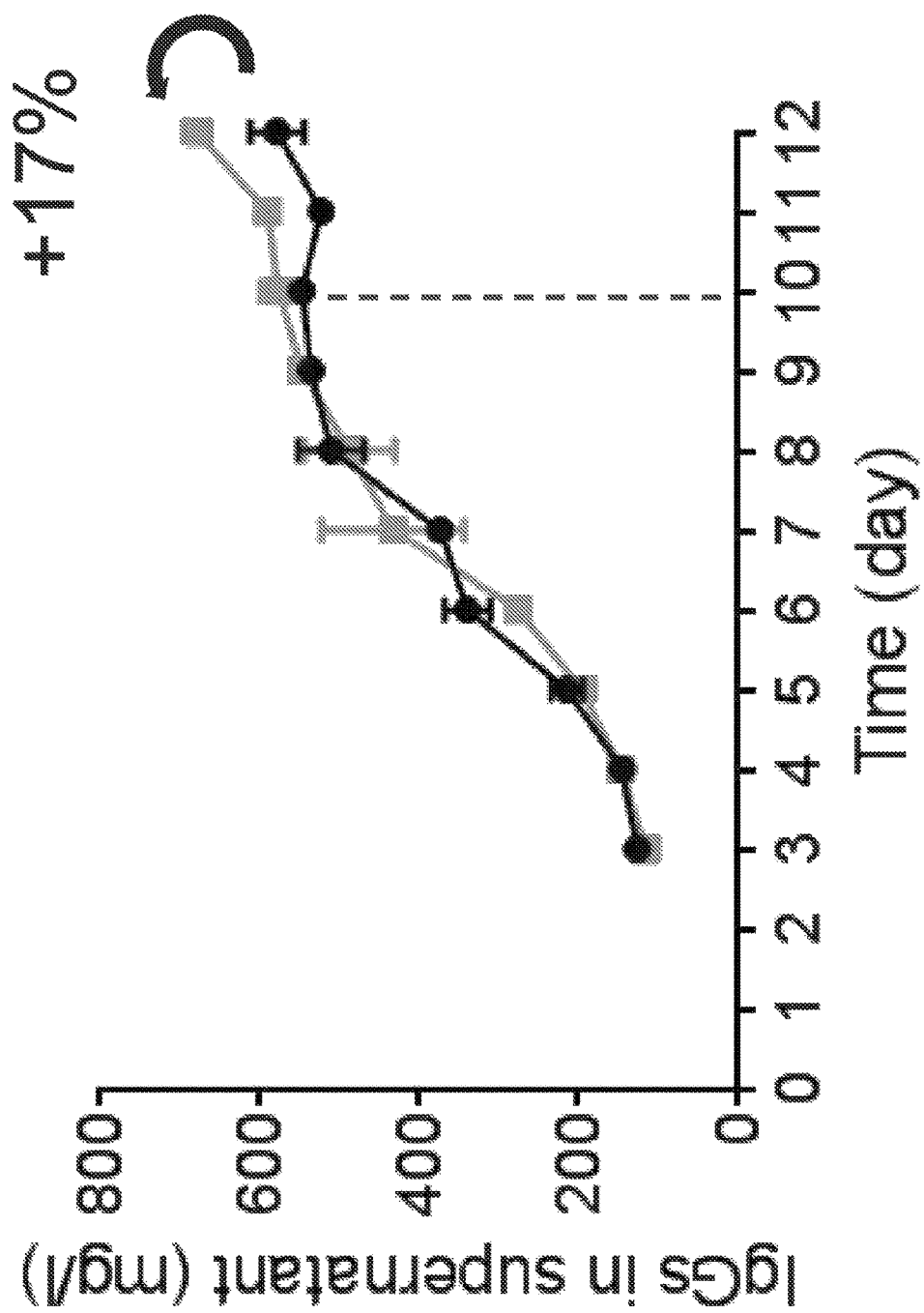
FIG. 6 shows the antibody titer for the cell cultures of FIG. 5.
Figure 7:
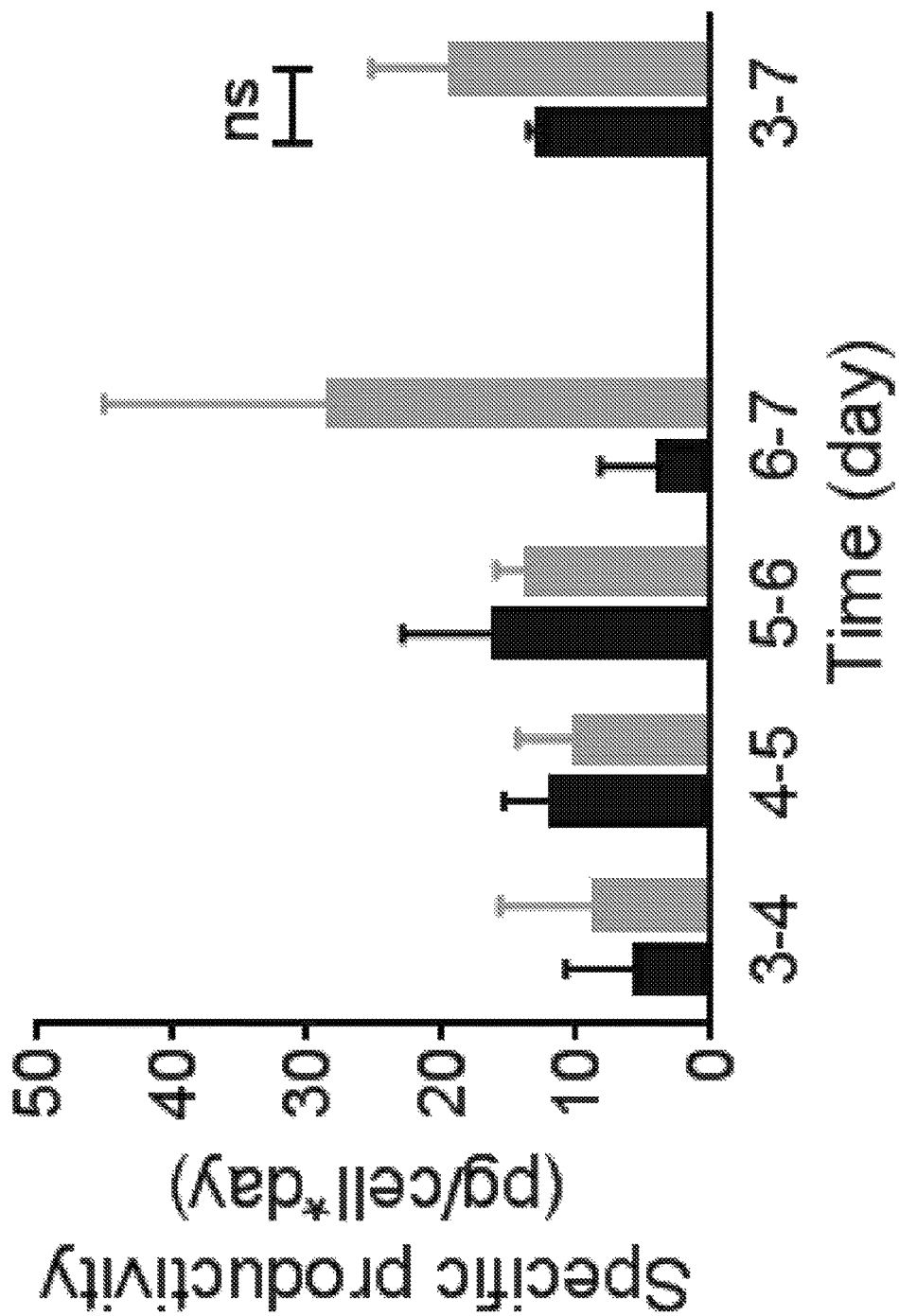
FIG. 7 shows the calculated specific cellular productivity for the cell cultures of FIG. 5.

Nitric Oxide (NO) is another Additive for inducing higher qP in eukaryotic cells such as the commonly used mammalian cell line, Chinese hamster ovary cells. FIGS. 5-7 show representative results from NO sparging experiments. In batch 3 L bioreactor cultures, screening of various concentrations demonstrated that optimal gaseous NO levels in the gas feed shifted the cell culture VCD profile and boosted qP similar to Carbon Monoxide. However, NO is shown to be a better single Additive in this context in that the VCD/qP balance produces a net culture yield increase of greater than 10%, generally approximately 20%, over control yields for the experimental batch cultures in 3 L bioreactors. A single molecule Additive is preferred for many reasons such as reducing the complexity of DoE optimizations and higher feasibility of any applicable regulatory approval. It is expected that further DoE optimization of culture conditions (e.g. Fed-Batch culturing), will improve overall antibody yield further.

Figure 8:
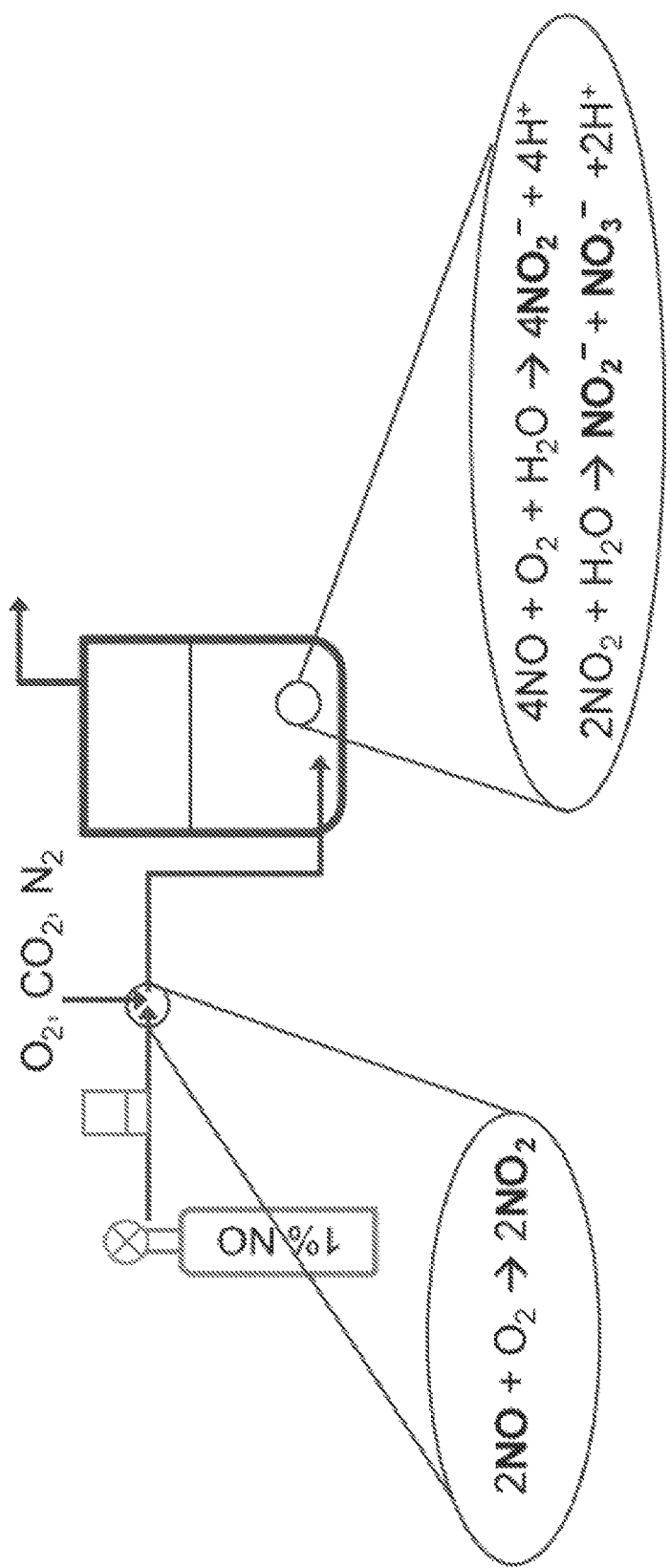
FIG. 8 shows the main chemical reaction/breakdown products produced by NO in the sparging gas and in the cell culture medium for the 3 L bioreactor batch cell culture format used for the experiments represented by FIGS. 5-7.

Nitric Oxide is not stable in cell culture media or even the sparging gas due to oxidation by oxygen gas (FIG. 8). Thus, in solution, sparging with NO delivers a combination of chemicals into the cell culture medium.

Sparged Cell Culture

We determined the levels of Nitric Oxide and its reaction products in the cell culture media as follows:

NO is mixed with $O_2$, $CO_2$, and $N_2$ before being delivered to the bioreactor. This configuration allows NO to react with $O_2$ and produce $NO_2$ ($2NO + O_2 \rightarrow 2NO_2$) before entering the bioreactor. Whereas the NO flow rate is maintained constant with a mass flow controller, $O_2$ flow changes according to the oxygen demand by cells, resulting in variations in NO and $NO_2$ concentrations entering the bioreactor over time.

In order to estimate NO and $NO_2$ concentrations, gas samples were collected from the entry line and quantified by SIFT-MS. It was concluded that concentrations of NO ranging from 120 to 250 ppm, and concentrations of $NO_2$ ranging from 50 to 200 ppm were delivered to the bioreactor during the experiment. Similarly, NO and $NO_2$ concentration in the outlet were measured. NO was found to range from 120 to 220 ppm, whereas $NO_2$ ranged from 50 to 100 ppm.

Figure 11:
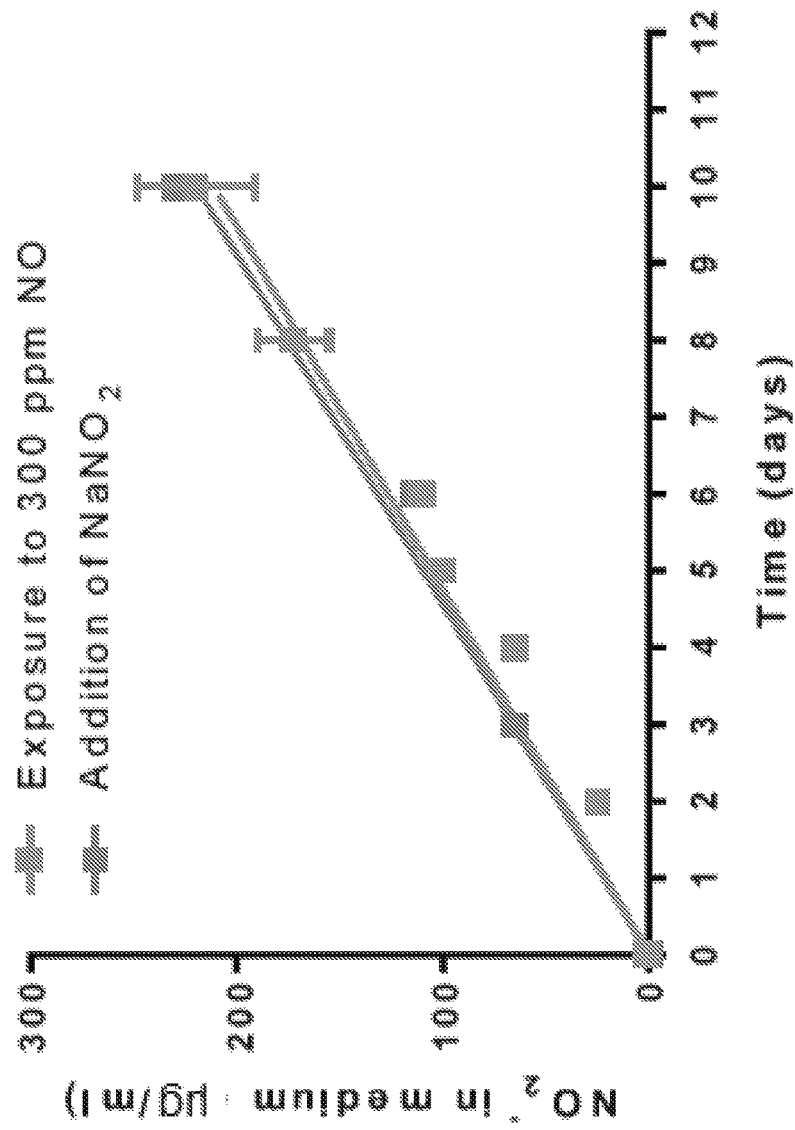
FIG. 11 shows the time course accumulation of Nitrite in batch 3 L cultures of CHO-HSB cells exposed to Nitric Oxide ("NO") gas supplied at 300 ppm on the cell culture sparging gas and the matching concentration profile for Nitrite in the Sodium Nitrite treated 3 L cell batch cultures.

To characterize nitrogen uptake into the culture media, production of nitrite or nitrate were monitored. These two species are formed following the reactions $4NO+O_2+2H_2O \rightarrow 4NO_2^-+4H^+$ and $2NO_2+H_2O \rightarrow NO_2^-+NO_3^-+2H^+$. NO and $NO_2$ were transferred at a relatively linear rate in the liquid medium described by the equation nitrite=23.12*time (FIG. 11). Nitrate was detected starting at day 5, and reached values close to 100 mg/L at the end of the culture.

The concentration of NO dissolved in the medium was determined both indirectly and directly. Due to its short half-life in a biological system, NO concentration is commonly estimated based on nitrite and nitrate. To obtain a direct measurement of NO in medium, four bioreactors were sparged with 300, 600, 900, or 1200 ppm NO for 24 hours. Nitrite concentration in the medium correlated with concentration of inlet gas. In the reactor sparged with 1200 ppm NO, NO was found at 120 nM in the medium, whereas at lower flow rates, the concentration of NO was in the low nanomolar range. These data indicate that in bioreactors sparged with 300 ppm NO, cells experience NO concentrations in the low (0.1-10) nanomolar range. These values are lower than those reported for cellular responses (Ignarro, L. J., 1990. Biosynthesis and metabolism of endothelium-derived nitric oxide. Annual review of pharmacology and toxicology, 30(1), pp. 535-560).

DETA-NO in Shake Flasks

Cells were grown in CDM4MAb medium supplemented with poloxamer-188. Flasks were incubated on a shaker at 125 rpm in a humidified incubator at 37° C. and 5% $CO_2$. DETA-NO was dissolved in 0.01 M sodium hydroxide solution at a 0.2 M concentration. Aliquots of DETA-NO solution were added daily to cell cultures to reach a final concentration of 0.09, 0.18 or 0.36 mM DETA-NO. Sodium hydroxide solution (0.01M) was added daily as a negative control. 0.01-1.0 mM DETA-NO release NO at a rate in the low nM/sec range (Bouton, C. and Demple, B., 2000. Nitric oxide-inducible expression of heme oxygenase-1 in human cells translation-independent stabilization of the mRNA and evidence for direct action of nitric oxide. Journal of Biological Chemistry, 275(42), pp. 32688-32693).

The three primary derivatives from gaseous NO in the medium are Nitrogen Dioxide, Nitrate and Nitrite (FIG. 8). We thus tested each of these as candidate Additives based on calculated concentrations of these chemical species in the NO sparged cell cultures.

Figure 9:
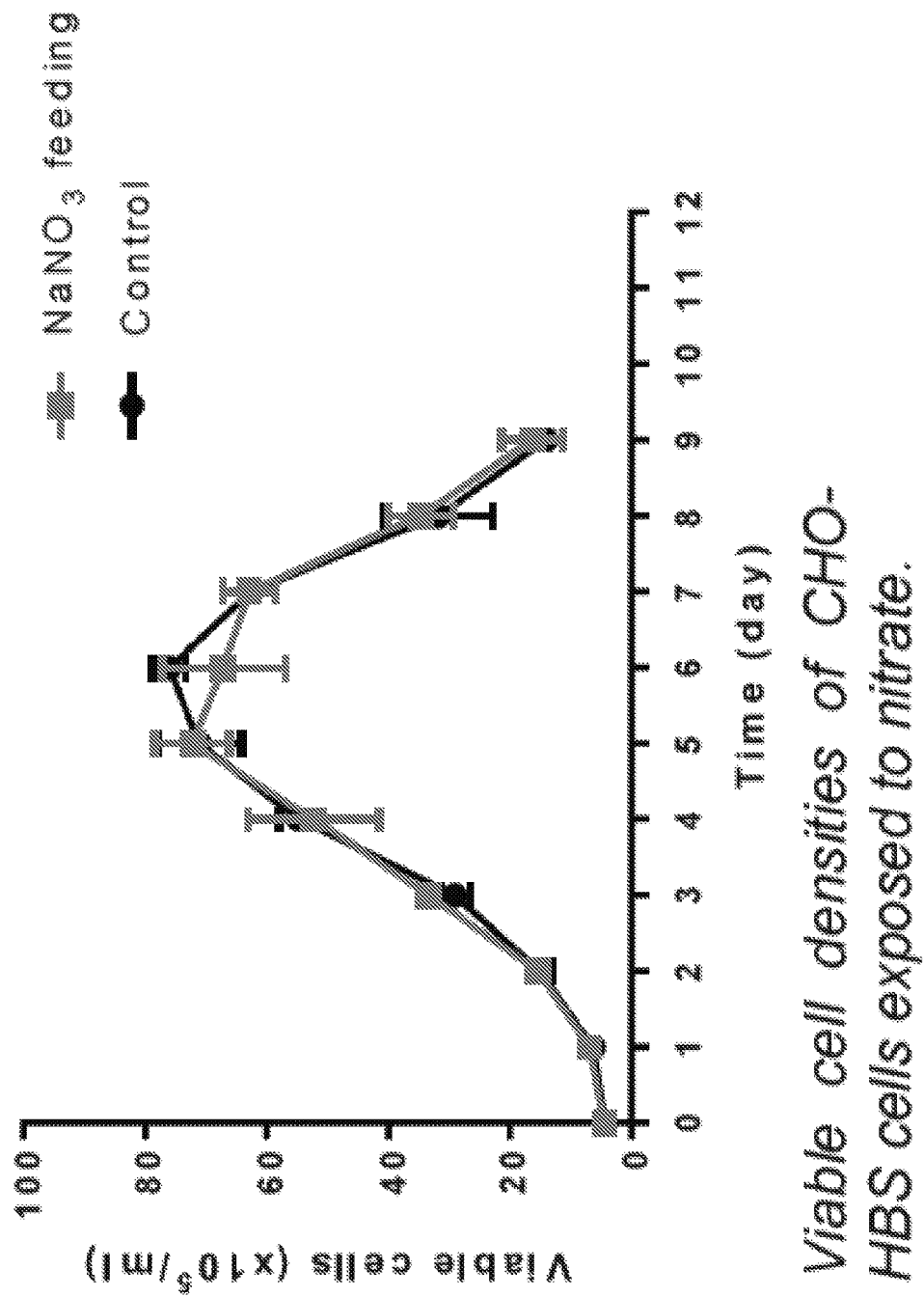
FIG. 9 shows the viable cell densities for 3 L batch cell cultures CHO-HSB cells exposed to Nitrate in the form of Sodium Nitrate added to the cell culture medium.
Figure 10:
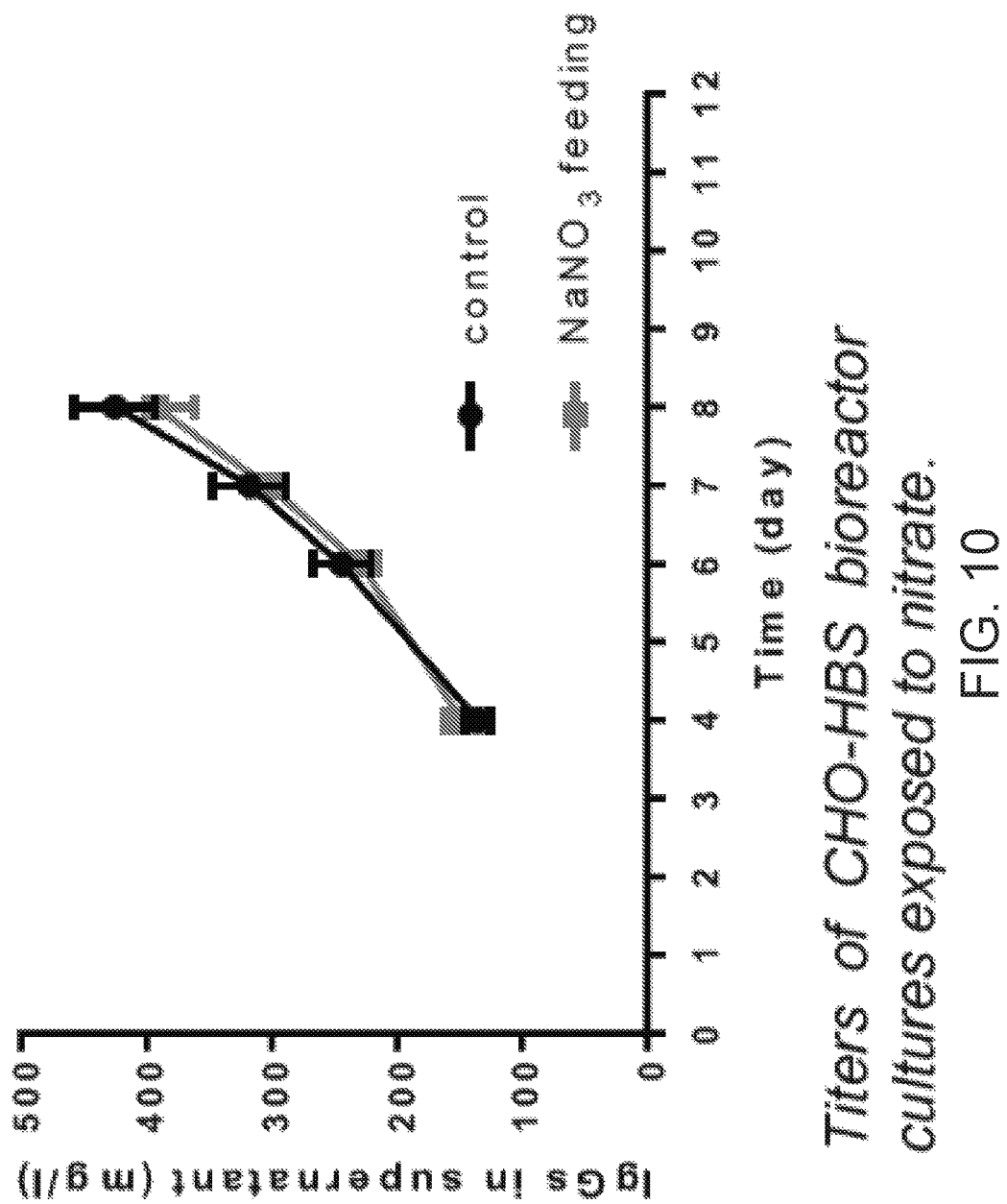
FIG. 10 shows the antibody titers for the 3 L batch cell cultures CHO-HSB cells exposed to Nitrate (same cultures as FIG. 9)

Sodium Nitrate (Dissolved):

Nitrate has no effect on VCD or antibody titers (FIGS. 9 and 10).

Figure 12:
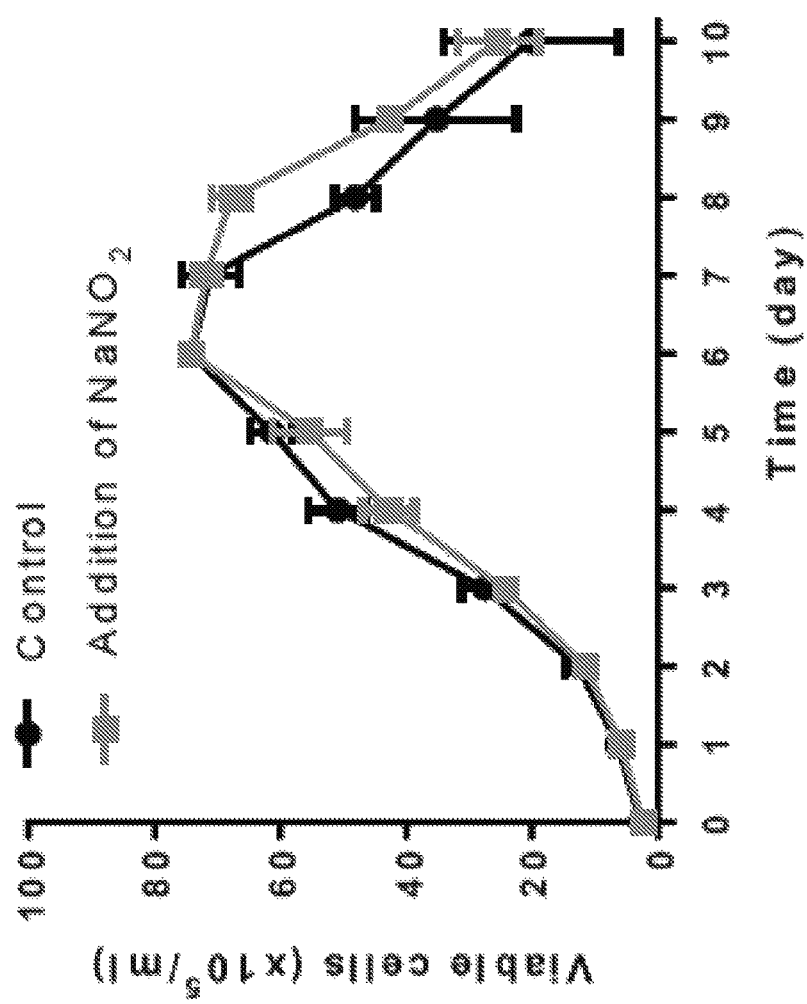
FIG. 12 shows the viable cell densities for 3 L batch cell cultures CHO-HSB cells exposed to Nitrite in the form of Sodium Nitrite added to the cell culture medium.
Figure 13:
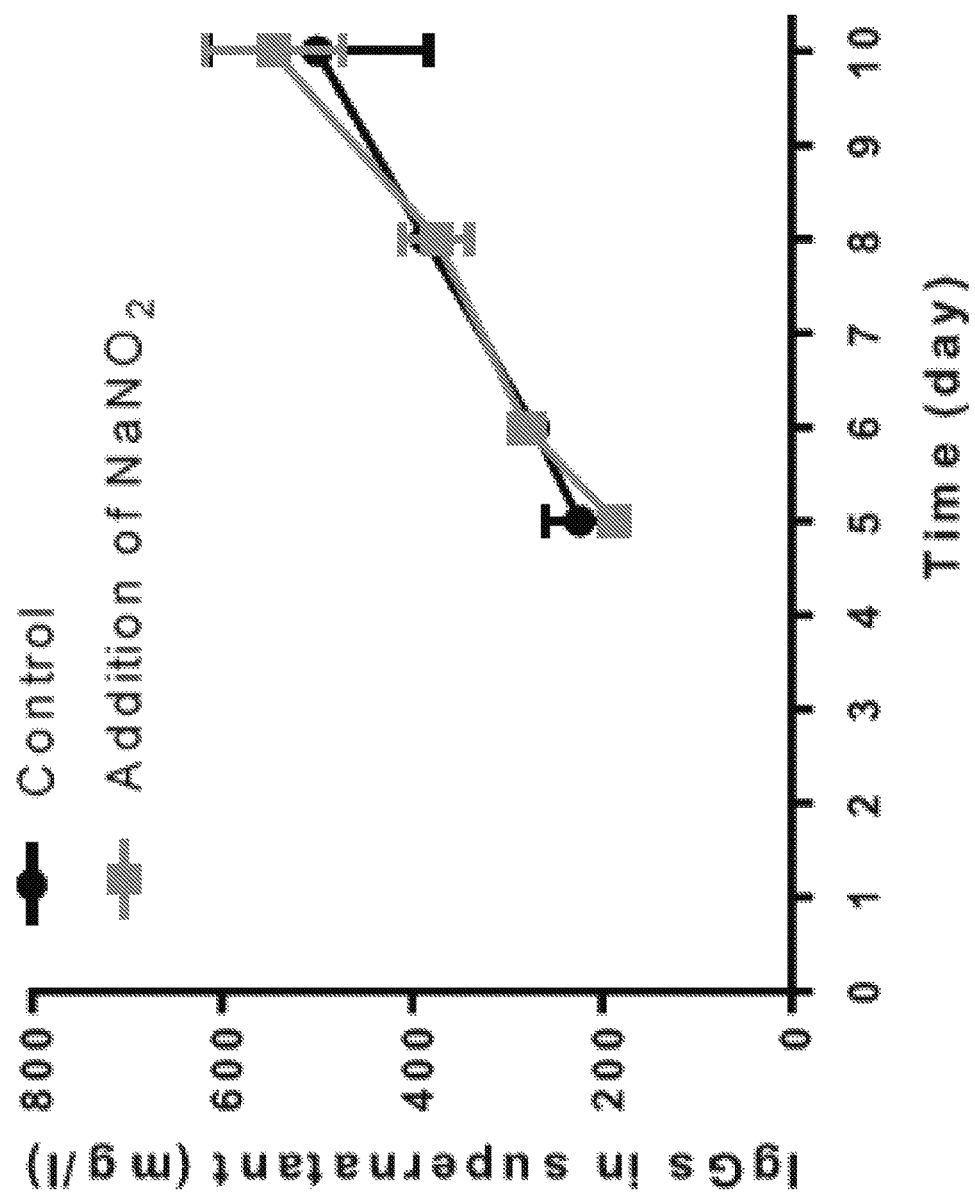
FIG. 13 shows the antibody titers for the 3 L batch cell cultures CHO-HSB cells exposed to Nitrite (same cultures as FIG. 12)
Figure 14:
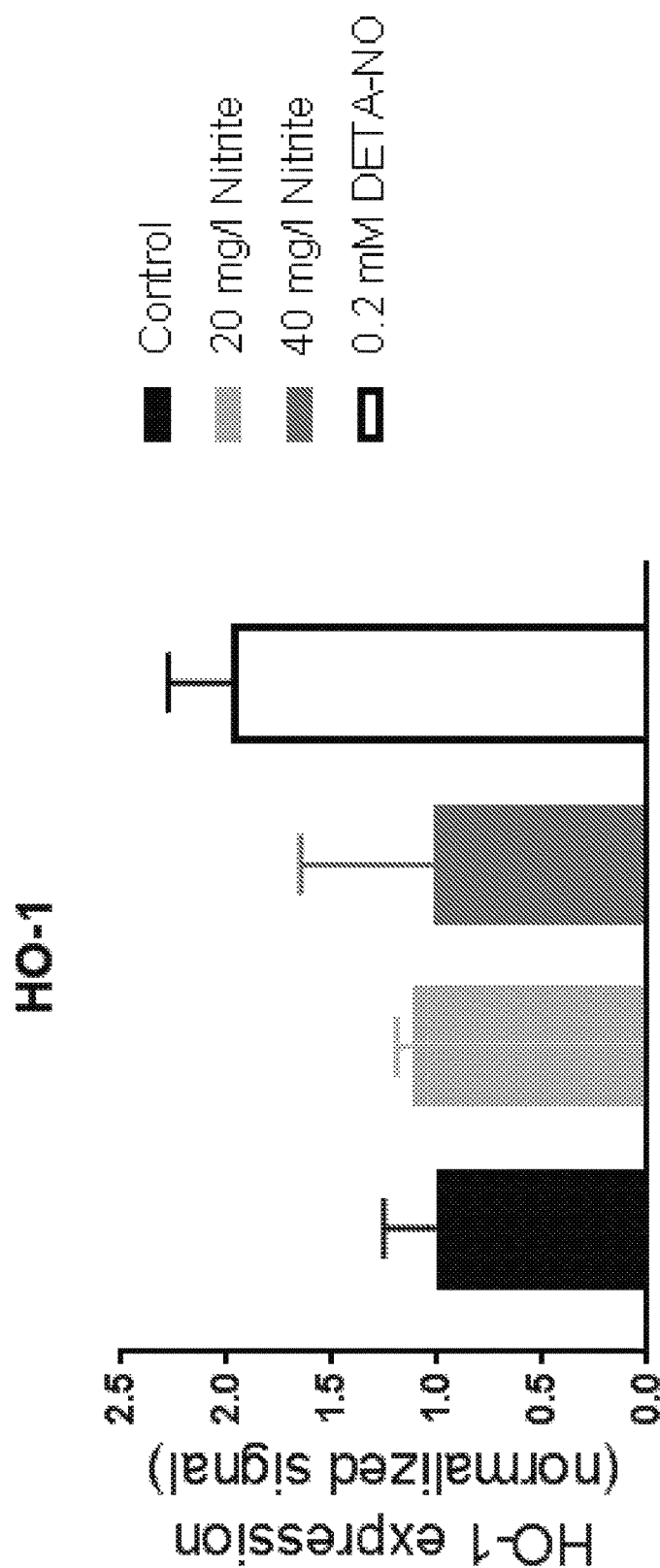
FIG. 14 shows normalized expression profiles for HO-1 expression in shake flask cultures comparing control cultures to Nitrite treated cultures and the positive control Nitric Oxide treated shake flask cultures (using DETA-NO as the source of Nitric Oxide)
Figure 15:
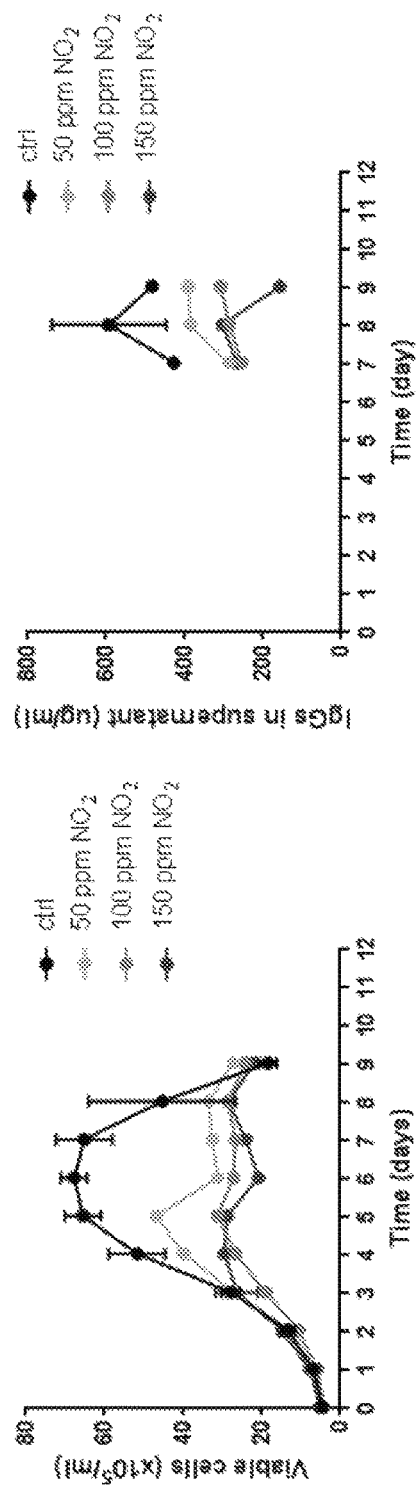
FIG. 15 shows viable cell culture densities and titers from batch 3 L cultures of CHO-HSB cells exposed to Nitrogen Dioxide gas in the sparging gas.

Sodium Nitrite (Dissolved):

Nitrite has at most a small effect on VCD in the late phase of culture with no significant impact on antibody titers (FIGS. 11-13). In contrast to nitric oxide, nitrite does not activate genes of the oxidative stress response, such as HO-1, based on relative expression levels in shake flasks using the Nitric Oxide producing chemical DETA-NO as the positive control (FIG. 14). Nitrogen Dioxide (gaseous): Nitrogen Dioxide, matched to produce comparable media concentrations as experienced by Nitric Oxide gas sparged cell cultures, has a strongly negative effect on VCD and antibody titer throughout the culture timeline (FIG. 15).

Based on these experiments with nitrogen dioxide, nitrate, and nitrite, the active molecule for the VCD and qP effect seen with NO gas sparging of the cell culture media is the NO molecule itself.

Nitric Oxide Gene Expression Profiling

Gene expression profiles were captured using RNA-seq. Conesa A, Madrigal P, Tarazona S, et al. A survey of best practices for RNA-seq data analysis. Genome Biology. 2016; 17:13. doi:10.1186/s13059-016-0881-8. RNA was extracted with a RNeasy Plus Mini kit (Qiagen) and quantified by absorbance at 260 nm with a NanoDrop 2000 (Thermo Fisher Scientific). The RNA quality was assessed using a RNA 6000 Nano Kit (Agilent) and a Bioanalyzer (Agilent). RNA was fragmented and libraries were prepared using commercial kits (TruSeq RNA Library Prep Kit v2, Illumina). RNA was sequenced on a HiSeq 2500 (Illumina) at the DNA Sequencing & Genotyping Center of the University of Delaware. Data were analyzed at the Bioinformatics Core Facility, Center for Bioinformatics and Computational Biology of the University of Delaware. As the specific genome sequence of the CHO DG44 line was not available, a Chinese Hamster genome draft was used as a reference. Genes with differential expression (false discovery rate <0.001) were further analyzed with DAVID 6.8 (https://david.ncifcrf.gov/), STRING 10.0 (http://string-db.org/) and iProXpress (http://pir.georgetown.edu/iproxpress2/).

Figure 17:
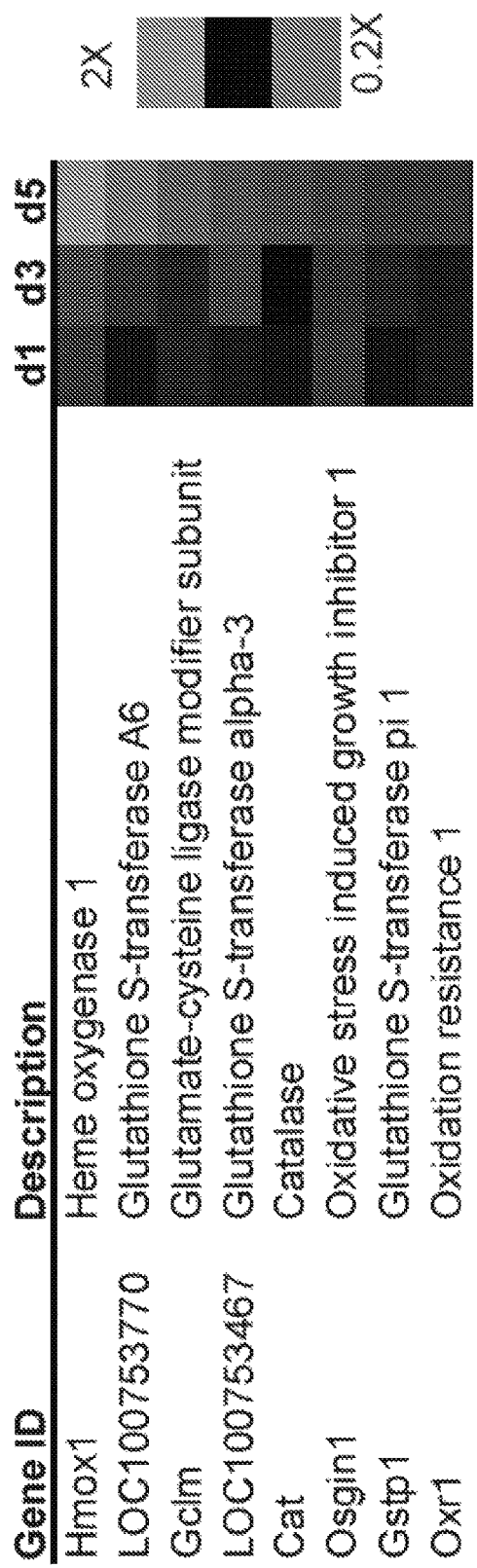
FIG. 17 table and heat map showing the genes with unregulated expression due to Nitric Oxide exposure.

Exemplary transcript profiles of cells on days 1, 3 and 5 of 3 L cell cultures were generated between control and gaseous NO treated cultures to perform differential gene expression analysis (FIG. 16). Genes differentially expressed relate to oxidative stress responses included Heme Oxygenase 1 ("HO-1") (FIG. 17).

NO can oxidize intracellular molecules and thereby change the antioxidant levels within the cell, resulting in oxidative stress that potentially leads to membrane dysfunction, DNA damage and inactivation of proteins. Glutathione-associated metabolism is a major mechanism for cellular protection against agents which generate oxidative stress. Glutathione participates in detoxification at several different levels, and may scavenge free radicals, reduce peroxides or be conjugated with electrophilic compounds. Gene expression profiles show that NO stimulates expression of glutathione-related enzymes (S-transferase proteins, catalases, and oxidation resistance genes) (FIG. 17). Moreover, NO induces expression of heme-oxygenase), which protects cells from apoptotic cell death induced by oxidative stress.

Figure 18:
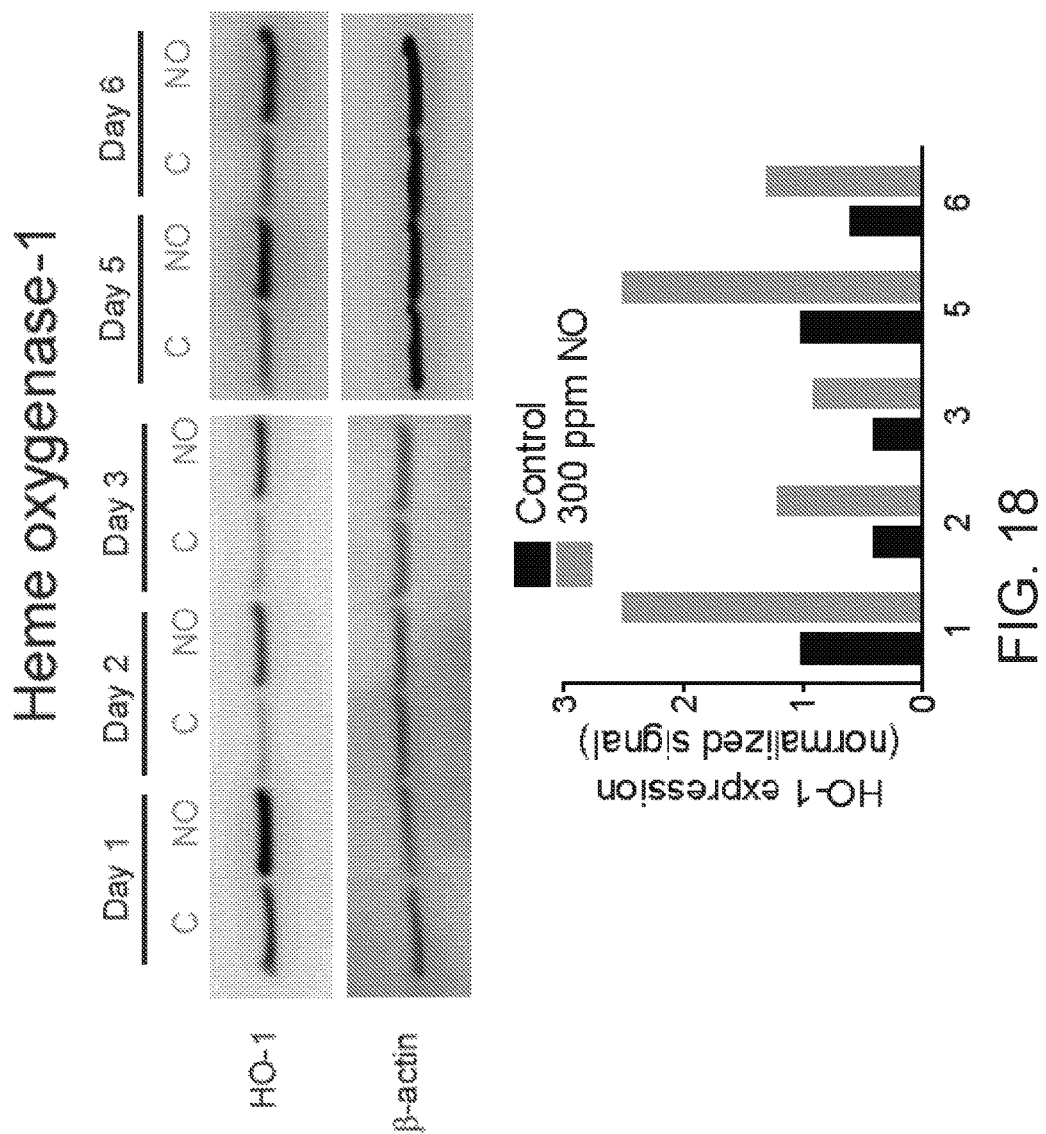
FIG. 18 shows Western Blot analysis and beta-actin normalized density readings for the HO-1 protein levels of cells from 3 L cultures of CHO-HSB cells exposed to NO gas supplied at 300 ppm on the cell culture sparging gas.
Figure 19:
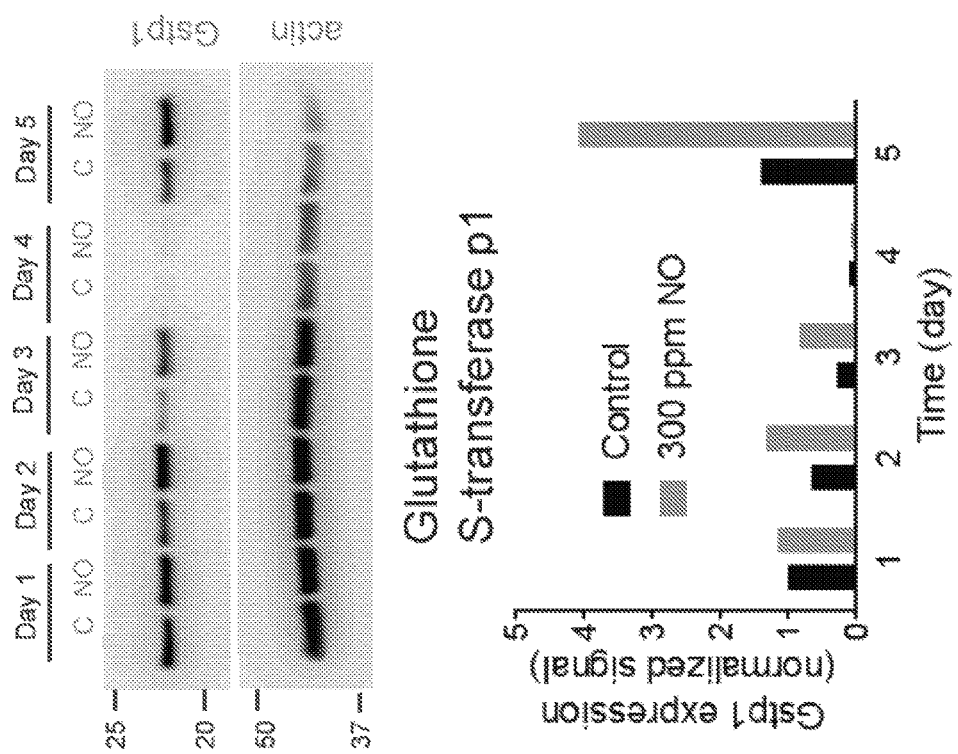
FIG. 19 Western Blot analysis and beta-actin normalized density readings for the Glutathione S-transferase p1 protein levels of cells from 3 L cultures of CHO-HSB cells exposed to NO gas supplied at 300 ppm on the cell culture sparging gas.

The differential transcription of HO-1 and various glutathione related genes were confirmed to correlate with increased translation and protein levels by Western blot analysis (FIG. 18-19). Expression and translation precede the timing of divergence in VCD between control and NO treated 3 L cell cultures.

Figure 20:
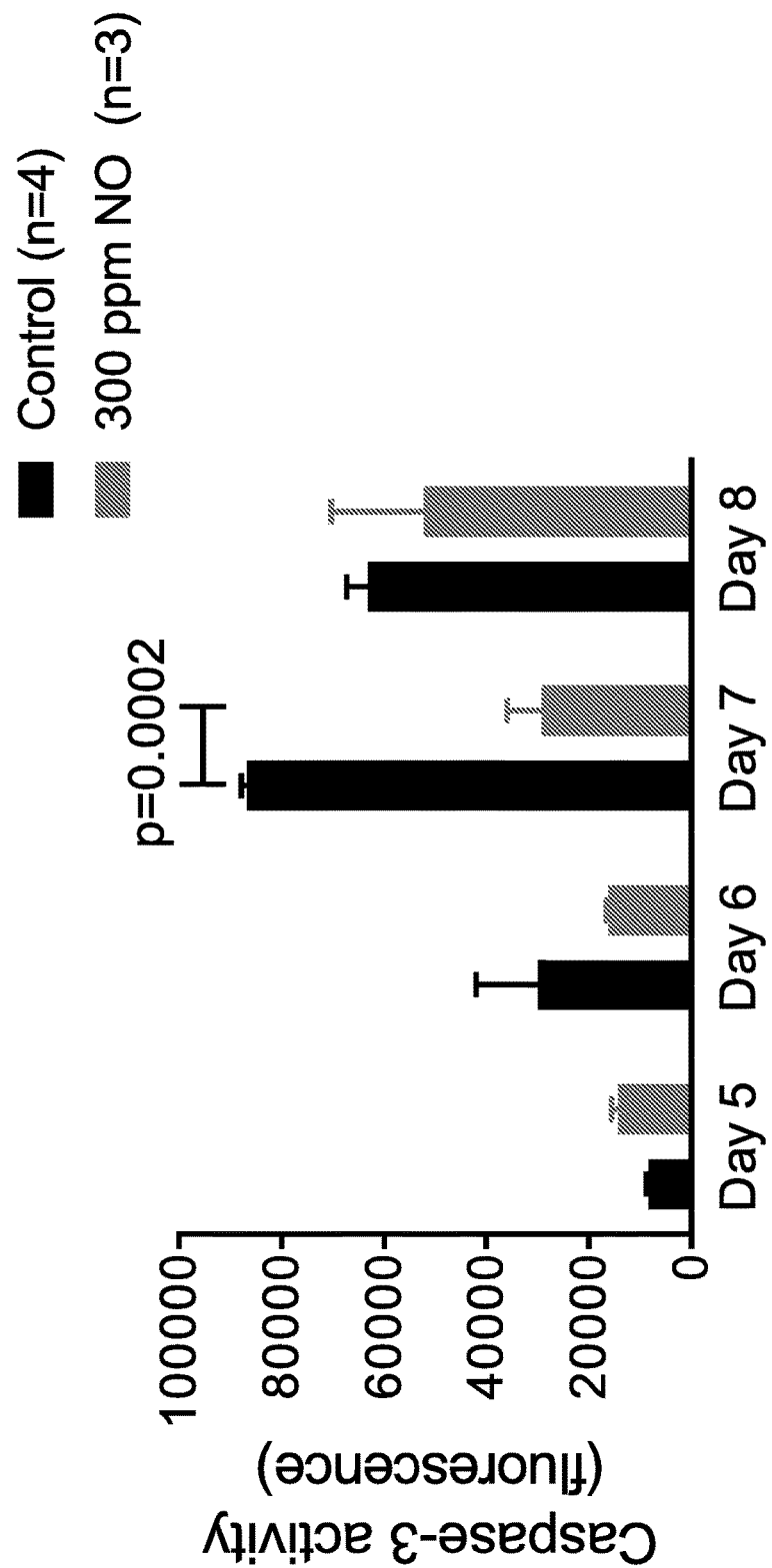
FIG. 20 shows Caspase-3 activity as measured by florescence intensity for and 3 L cultures of CHO-HSB cells±Nitric Oxide ("NO") gas supplied at 300 ppm on the cell culture sparging gas.

The NO-specific extension of viability correlates with a decrease in Caspase-3 activity (FIG. 20). Capase-3 activity was monitored with an EnzCheck Caspase-3 Assay Kit #1 (Thermo Fisher Scientific) using samples containing the same number of viable cells. All caspase proteases contain a single cystein at the enzyme catalytic site that is essential for activity. The thiol is susceptible to redox modification and can be efficiently nitrosylated in the presence of NO, leading to reduction of caspase activity (Li, J., Billiar, T. R., Talanian, R. V. and Kim, Y. M., 1997. Nitric oxide reversibly inhibits seven members of the caspase family via S-nitrosylation. *Biochemical and biophysical research communications*, 240(2), pp. 419-424). Thus, the observed lower caspase-3 activity may be due to a specific blockage of the catalytic cysteine residue through formation of nitrosylthiols. Inhibition of apoptosis may be also compatible with limited caspase processing from the pro-enzyme (inactive form), which has been demonstrated for caspase-3 (Mannick, J. B., Hausladen, A., Liu, L., Hess, D. T., Zeng, M., Miao, Q. X., Kane, L. S., Gow, A. J. and Stamler, J. S., 1999. Fas-induced caspase denitrosylation. *Science*, 284(5414), pp. 651-654).

Nitric Oxide (Chemical)

Figures 21A, 21B:
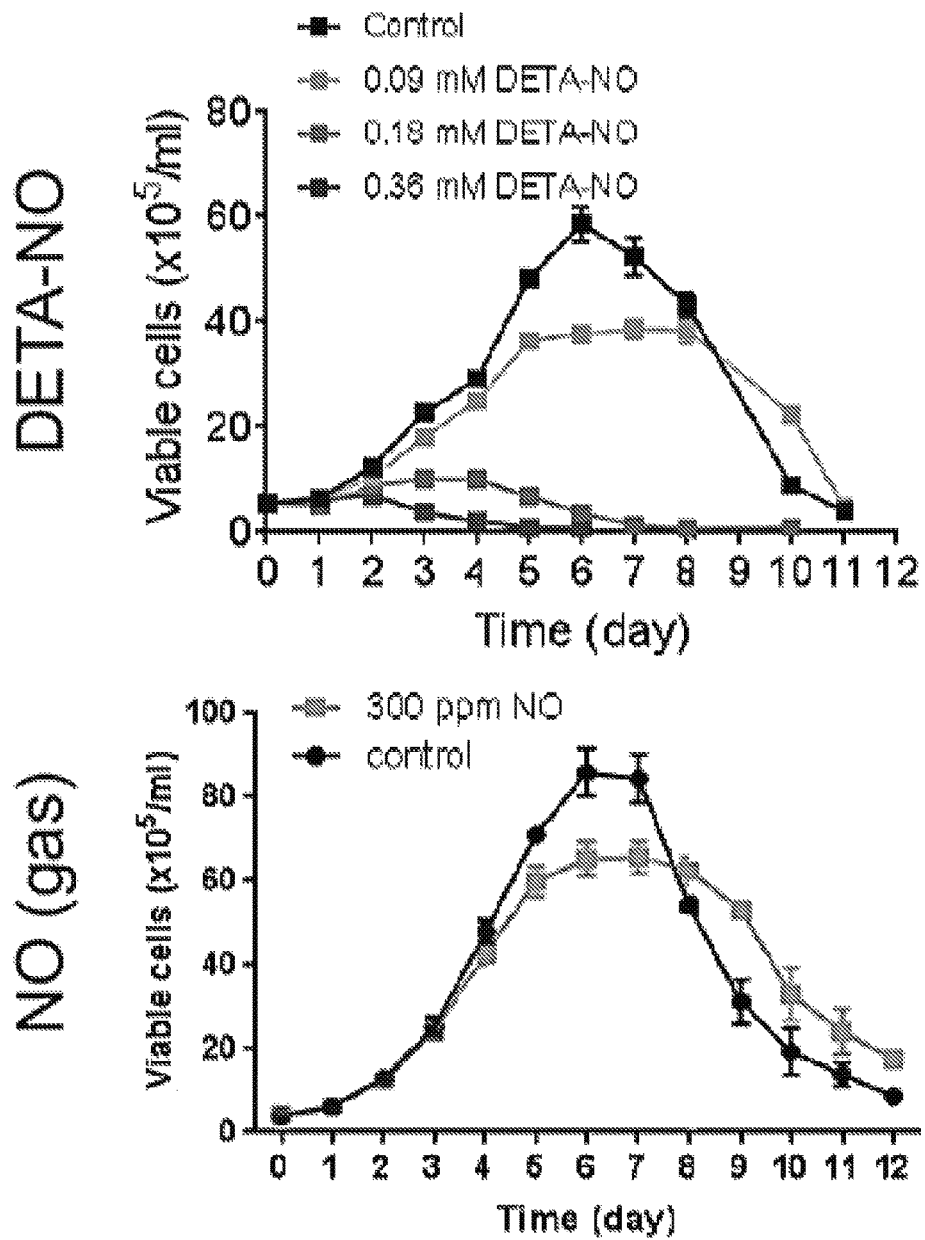
FIG. 21A shows viable cell densities for three DETA-NO concentrations (0.09 mM, 018 mM and 0.36 mM) shake flask cultures of CHO-HSB cells.
FIG. 21B shows representative date from 3 L batch cultures of CHO-HSB cells exposed to NO gas supplied at 300 ppm on the cell culture sparging gas.
Figures 22A, 22B:
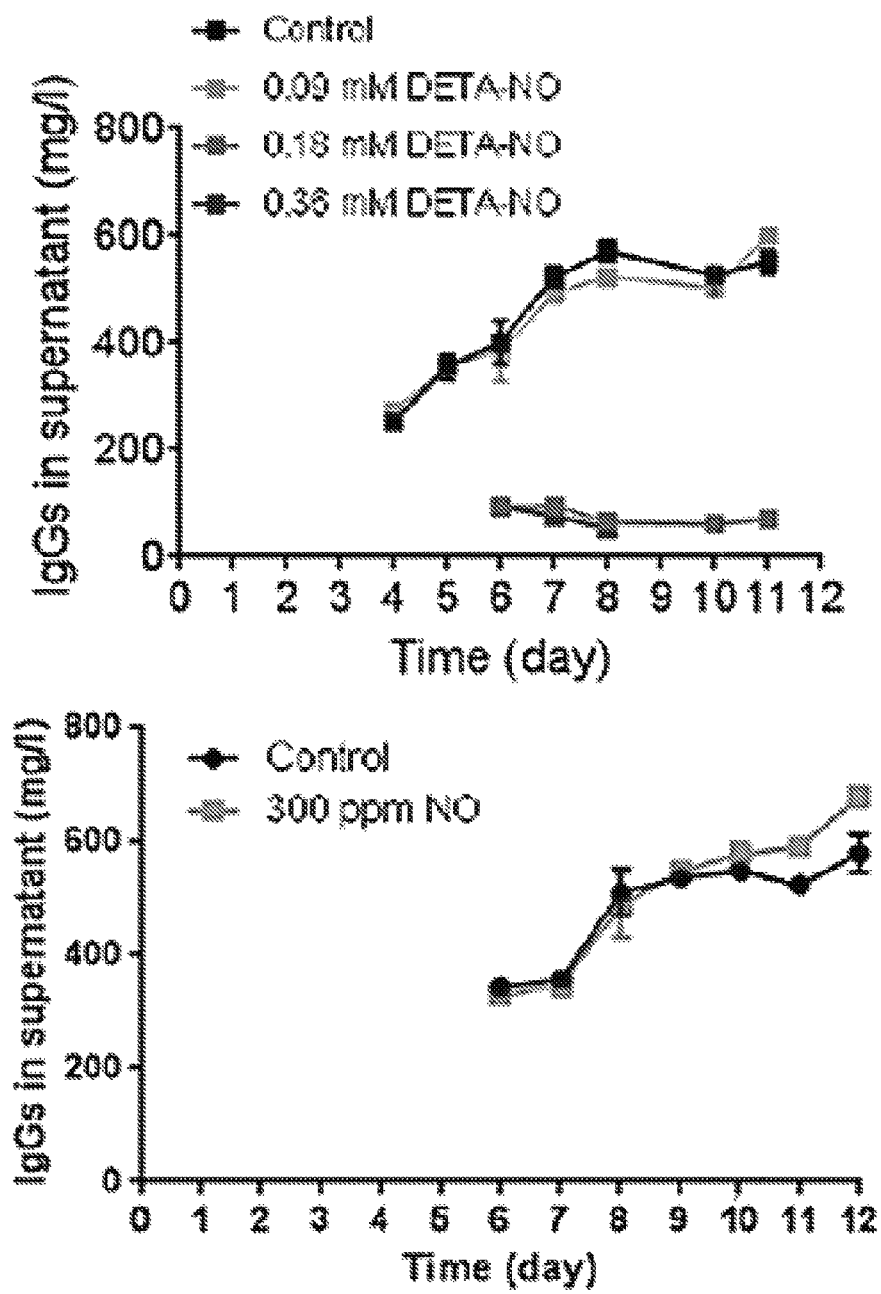
FIG. 22A shows antibody titers for 3 L NO sparged cell culture data from the cell cultures shown in FIG. 21.
FIG. 22B shows antibody titers for the DETA-NO shake flask experiments.
Figure 23:
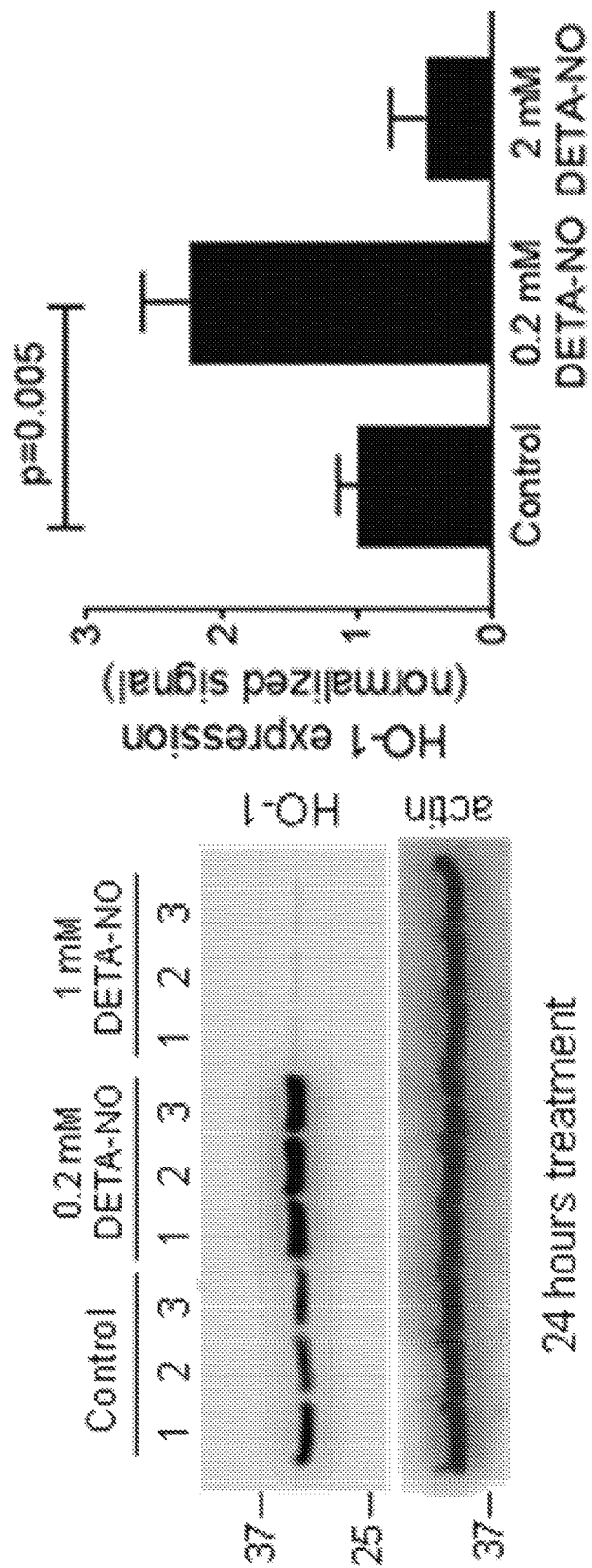
FIG. 23 shows Western Blot and beta-actin normalized densitometry values for HO-1 protein expression in DETA-NO treated CHO-HSB cells from shake flask cultures.

The effects of gaseous NO were partially recapitulated by adding NO-releasing compound DETA-NO daily to cell cultures in shake flasks. Cell growth and viability followed similar trends with addition of DETA-NO as with gaseous NO. In both cases, viable cell counts were lower at the stationary phase but increased in the late phase of the culture, relative to control cultures. As for gaseous NO, incubation with the higher concentrations of DETA-NO tested also resulted in increased cell death (FIG. 21-22). Incubation with the lower tested doses of DETA-NO also activated an oxidative stress response, as demonstrated by HO-1 up regulation (FIG. 23).

Cells & Biomolecules Tested

CHO HBsAb—An HBS antibody producing CHO (CHO-HBS) recombinant cell line was obtained from the G. M. Lee laboratory at the Korea Advanced Institute of Science and Technology. Kim, S. J., Kim, N. S., Ryu, C. J, Hong, H. J, Lee, G. M. 1998. Characterization of Chimeric Antibody Producing CHO Cells in the Course of Dihydrofolate Reductase-Mediated Gene Amplification and Their Stability in the Absence of Selective Pressure. *Biotechnology and Bioengineering*, Vol. 58, No. 1, Apr. 5, 1998. Page 73-84.

CHO EPO—An erythropoietin (EPO) producing CHO (CHO-EPO) recombinant cell line was obtained from the G. M. Lee laboratory at the Korea Advanced Institute of Science and Technology. This is the same cell line as CHO HBsAb that was modified for EPO production.

CHO-EPO Prophetic Example:

CHO-EPO cells will be cultured in 3 L cell culture bioreactors under conditions similar to CHO-HBS experiments, with optimization of standard conditions to achieve a baseline cell culture titer as a comparative control. Nitric Oxide gas will be evaluated to identify the optimal gas concentration based on VCD and overall culture titer/yield of EPO. The CHO-EPO cells will respond to Nitric Oxide to increase the yield of EPO relative to the control results.

Biomolecule Integrity

Antibody Assembly

Figure 24:
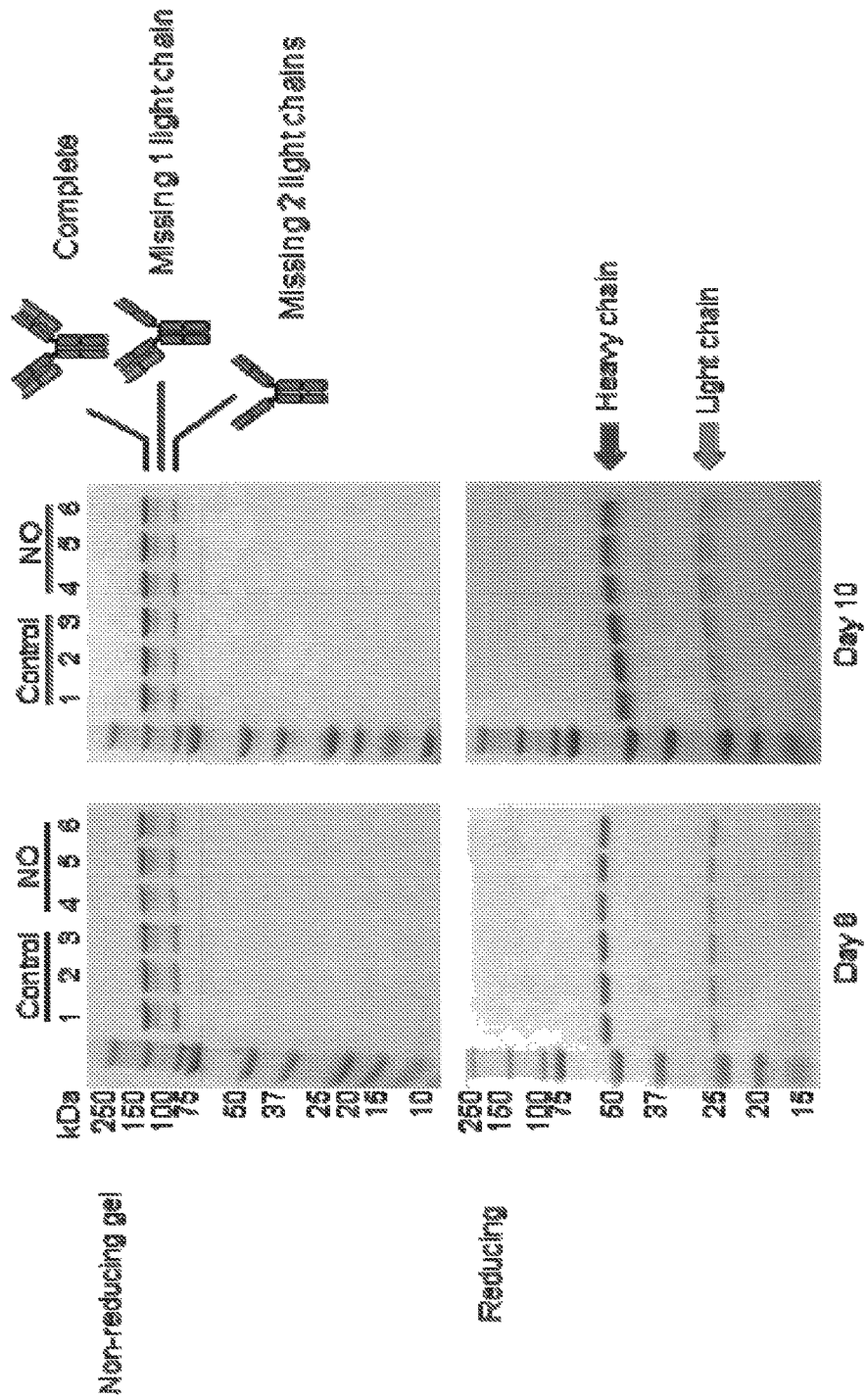
FIG. 24 shows IgGs purified from control bioreactors (lanes 1-3) or bioreactors sparged with 300 ppm NO (lanes 4-6) at day 8 or 10 separated by SDS-PAGE in the absence (top) or in the presence of reducing agents.

In the absence of reducing agents, the pool of IgGs consists of three structures: fully assembled IgGs, IgGs missing one light chain, and IgGs missing two light chains. Variations in the proportion of the three structures depend on the production process and intrinsic properties of the IgG molecules. NO did not seem to impact the overall IgG structure according to non-reducing SDS-PAGE (FIG. 24). In the presence of reducing agents, the three structures collapsed into two forms of approximately 52 and 26 kDa, corresponding to the heavy and light chains, respectively. No major differences were detected between antibodies produced in NO-sparged reactors compared to controls. Byproducts with an apparent molecular mass of 25 kDa were detected on day 10. These species, which might be degradation products of light chains, seemed to be an intrinsic feature of HBS antibodies independent from the NO-based process.

Binding to Antigen

Affinity to antigen was measured with an Octet instrument (ForteBio). Anti-HBS antibodies exhibited affinity values close to those originally reported. Ryu, C. J., Gripon, P., Park, H. R., Park, S. S., Kim, Y. K., Guguen-Guillouzo, C., Yoo, O. J. and Hong, H. J., 1997. In vitro neutralization of hepatitis B virus by monoclonal antibodies against the viral surface antigen. *Journal of medical virology*, 52(2), pp. 226-233. IgGs purified from reactors sparged with 300 ppm NO did not show changes in binding to the antigen (Table 1). Although samples obtained from NO treated reactors had lower $k_{OFF}$ and $K_D$ values on day 10 compared with control cultures, these differences were not statistically significant. Dissociation constants were in the low nanomolar values for both IgG products at day 8 and 10.

TABLE 1

Binding parameters for HBS IgG/antigen.
Average values and standard deviation are indicated, n = 3.

| | Time | Control | 300 ppm NO | Unpaired t test |
|---|---|---|---|---|
| $k_{ON}$ (M$^{-1}$ s$^{-1}$) | Day 8 | (1.4 ± 0.3) E+5 | (1.7 ± 0.4) E+5 | p = 0.28 |
| | Day 10 | (2.6 ± 0.7) E+5 | (2.5 ± 0.3) E+5 | p = 0.82 |
| $k_{OFF}$ (s$^{-1}$) | Day 8 | (1.1 ± 0.2) E−3 | (1.2 ± 0.3) E−3 | p = 0.76 |
| | Day 10 | (2.1 ± 0.3) E−3 | (1.3 ± 0.6) E−3 | p = 0.12 |
| $K_D$ (M) | Day 8 | (8.4 ± 3.3) E−9 | (7.2 ± 2.8) E−9 | p = 0.65 |
| | Day 10 | (8.4 ± 3.3) E−9 | (5.4 ± 2.8) E−9 | p = 0.27 |

Stability

IgGs were separated according to their apparent molecular weight by size-exclusion liquid chromatography with an Advance BioSEC 300 Å column (Agilent) using phosphate buffered saline as the mobile phase. The quality of separation was assessed by using protein standards (Advance SEC Protein standards, Agilent). IgG monomers appear to be the major species. Incomplete antibodies missing one or two light chains were found. Dimers and soluble aggregates were also detected at lower levels. In both control and NO-sparged reactors, the levels of aggregates and incomplete antibodies appear to increase over the culture time in a similar manner.

Figure 25:
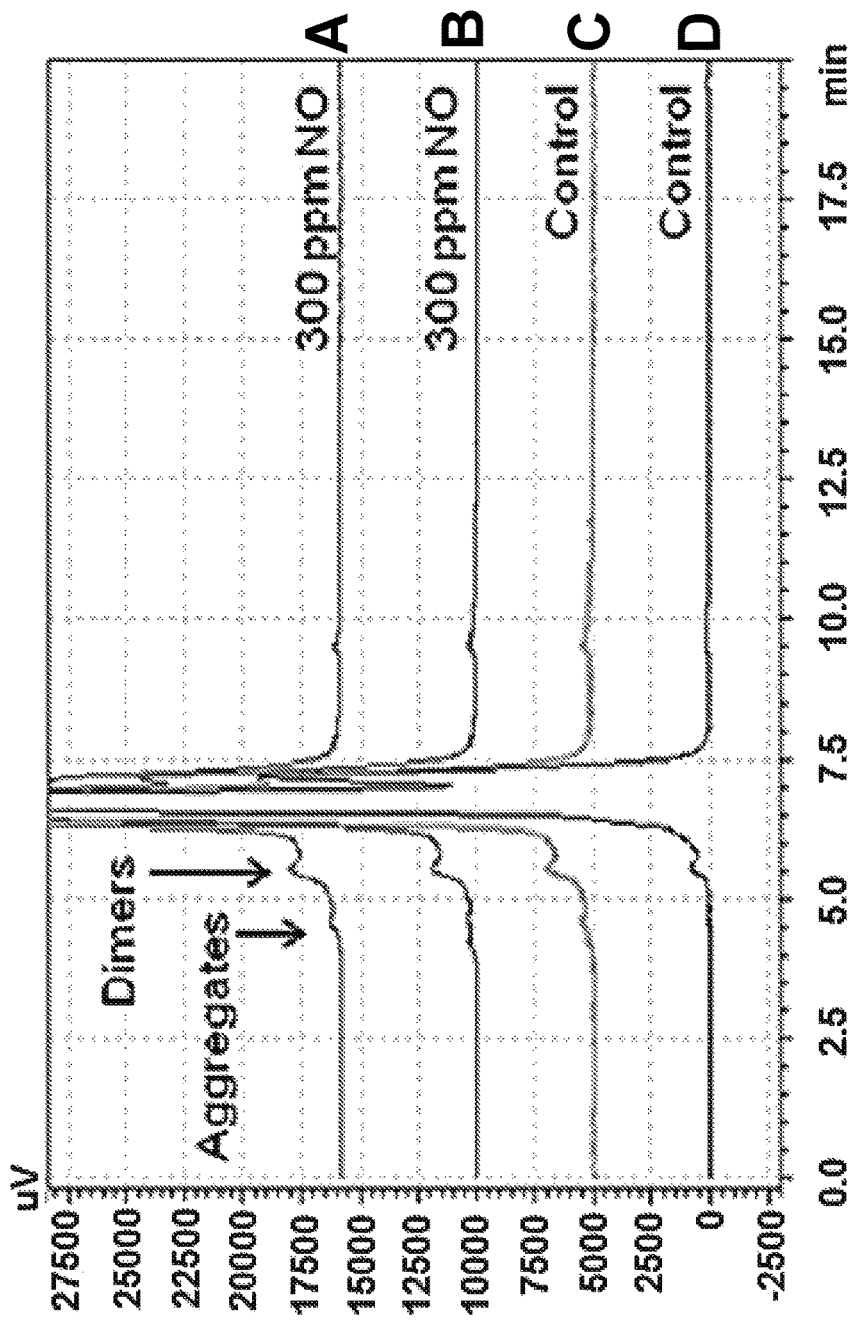
FIG. 25 shows Chromatograms of antibodies at day 10 of culture, highlighting dimeric forms and aggregates for two cultures treated with 300 ppm Nitric Oxide (A, B) and two control cultures (C, D)

The peaks corresponding to dimers and aggregates were comparable at day 10 of culture for NO-treated and control IgGs (FIG. 25). The only notable difference was a broadening of the peak corresponding to IgG monomers in antibody preparations from reactors sparged with NO. This phenomenon was visible in IgGs collected at day 5 and appeared to increase over time.

Glycosylation Analysis

Figure 26:
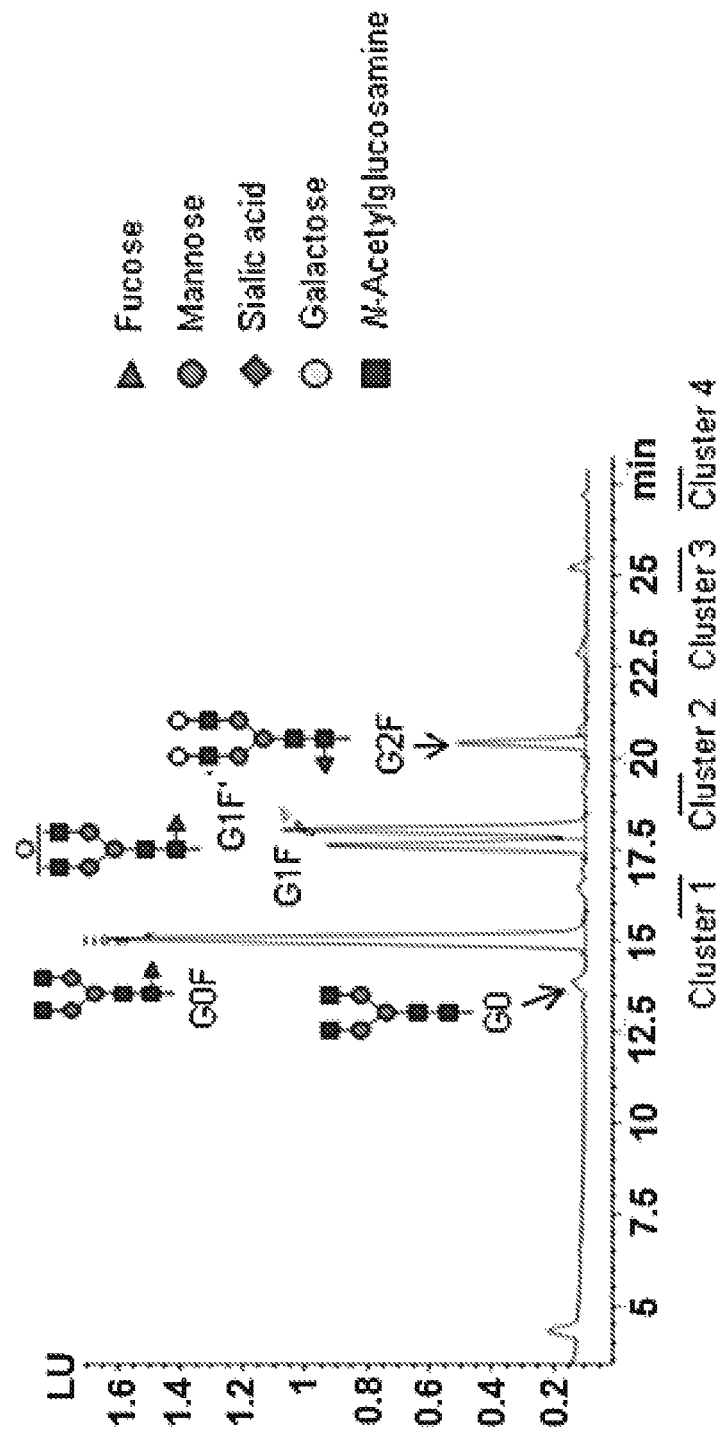
FIG. 26 shows typical glycan profiles of IgGs purified from untreated CHO-HBS cell cultures. G0, G0F, G1F, G1F', G2F and cluster 1-3 refer to the different types of glycans detected by HPLC. The main classes of glycans are also represented with colored geometric symbols.

Glycans were enzymatically released from purified IgGs, labeled with a fluorescent dye, and separated by hydrophilic interaction liquid chromatography (GlycoWorks RapiFluor-MS N-Glycan Kit, Waters). Glycans of IgGs purified from CHO-HBS cells were consistent with the typical patterns reported in the literature for proteins expressed in CHO cells. A heterogeneous population of glycans with high proportion of G0F structure followed by G1F and G2F was observed (FIG. 26).

Figure 27:
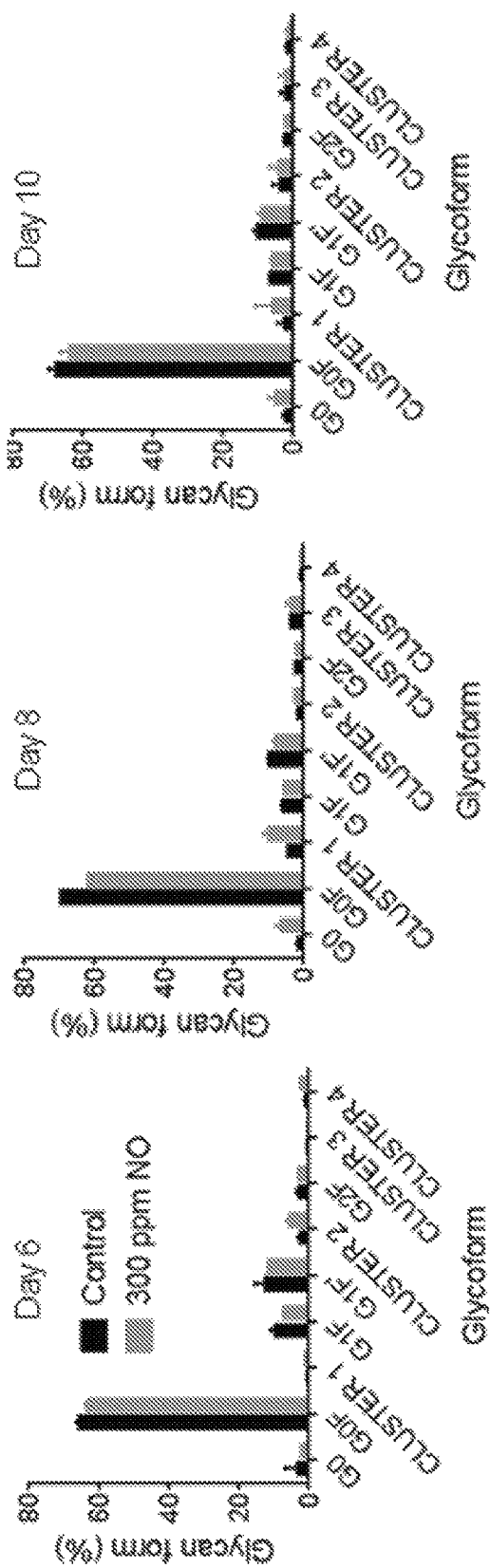
FIG. 27 shows comparative analysis of glycan structures of IgGs from control and bioreactors sparged with 300 ppm NO. Average and standard deviation is indicated for each sample (n=3 for day 6 and day 8 samples; n=6 for day 10 samples)

The major glycan form detected at day 6, 8 and 10 was the agalactosylated G0F form, followed by the monogalactosylated form G1F, both in NO-treated cultures and in controls (FIG. 27). Treatment of CHO-HBS cells with 300 ppm NO resulted in a minor reduction of fucosylated glycans.

Binding to Fc Receptor

Antibody association and dissociation rates to biotinylated Fc receptors (CD16a, CD32a or CD64) were measured on an Octet instrument (ForteBio). $K_D$ values obtained for the IgGs/Fc receptors were within the expected range (Gillis, C., Gouel-Chéron, A., JÖnsson, F. and Bruhns, P., 2014. Contribution of human FcγRs to disease with evidence from human polymorphisms and transgenic animal studies. *Frontiers in immunology*, 5, p. 254). CD32a and CD16a showed low to medium binding kinetics in the μM range, whereas CD64 had high affinity with $K_D$ values in the nanomolar range (Table 2). Antibodies obtained from cells treated with NO exhibited undistinguishable binding to CD32a and CD64, and increased affinity to human CD16a, compared to controls.

TABLE 2

Binding parameters for IgG/Fc receptors. Average values and standard deviation are indicated, n = 3

| Parameter | Receptor | Control | 300 ppm NO | T test |
|---|---|---|---|---|
| $K_D$ (M) | CD16a | (2.61 ± 0.06) E−07 | (1.68 ± 0.26) E−07 | p = 0.017 |
|  | CD32a | (1.59 ± 0.20) E−07 | (1.16 ± 0.15) E−07 | p = 0.04 |
|  | CD64 | (3.50 ± 3.00) E−09 | (1.14 ± 1.04) E−09 | p = 0.27 |
| $k_{ON}$ ($M^{-1} s^{-1}$) | CD16a | (5.92 ± 1.99) E+04 | (4.34 ± 0.24) E+04 | p = 0.24 |
|  | CD32a | (9.21 ± 1.58) E+04 | (6.04 ± 0.11) E+04 | p = 0.03 |
|  | CD64 | (1.73 ± 1.19) E+05 | (1.73 ± 0.72) E+05 | p = 0.99 |
| $k_{OFF}$ ($s^{-1}$) | CD16a | (1.23 ± 0.07) E−02 | (7.30 ± 1.22) E−03 | p = 0.003 |
|  | CD32a | (1.44 ± 0.11) E−03 | (5.47 ± 2.06) E−03 | p = 0.003 |
|  | CD64 | (3.36 ± 2.47) E−04 | (1.54 ± 0.79) E−04 | p = 0.29 |

Figure 28:
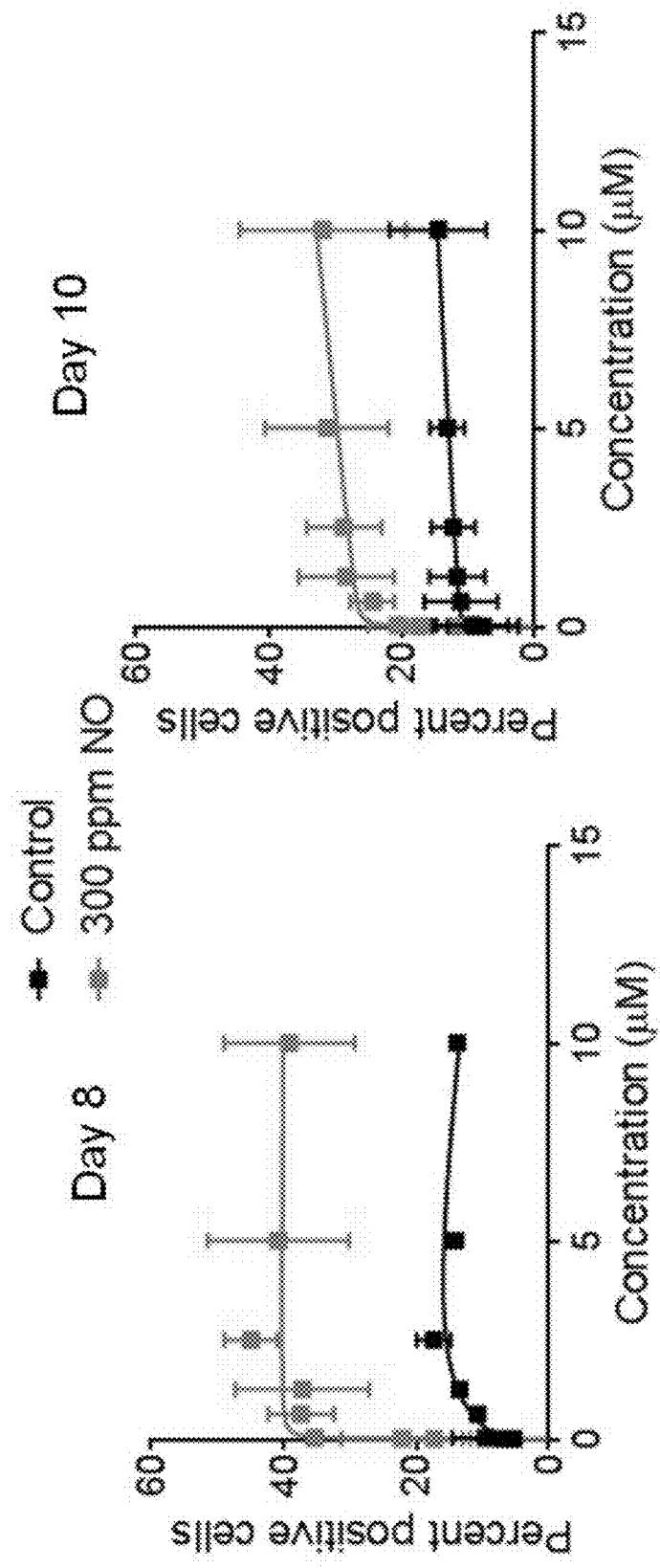
FIG. 28 shows antibody binding to cells expressing CD16a receptor as the percentage of fluorescently labeled cells at different concentrations of antibodies.
Figure 29:
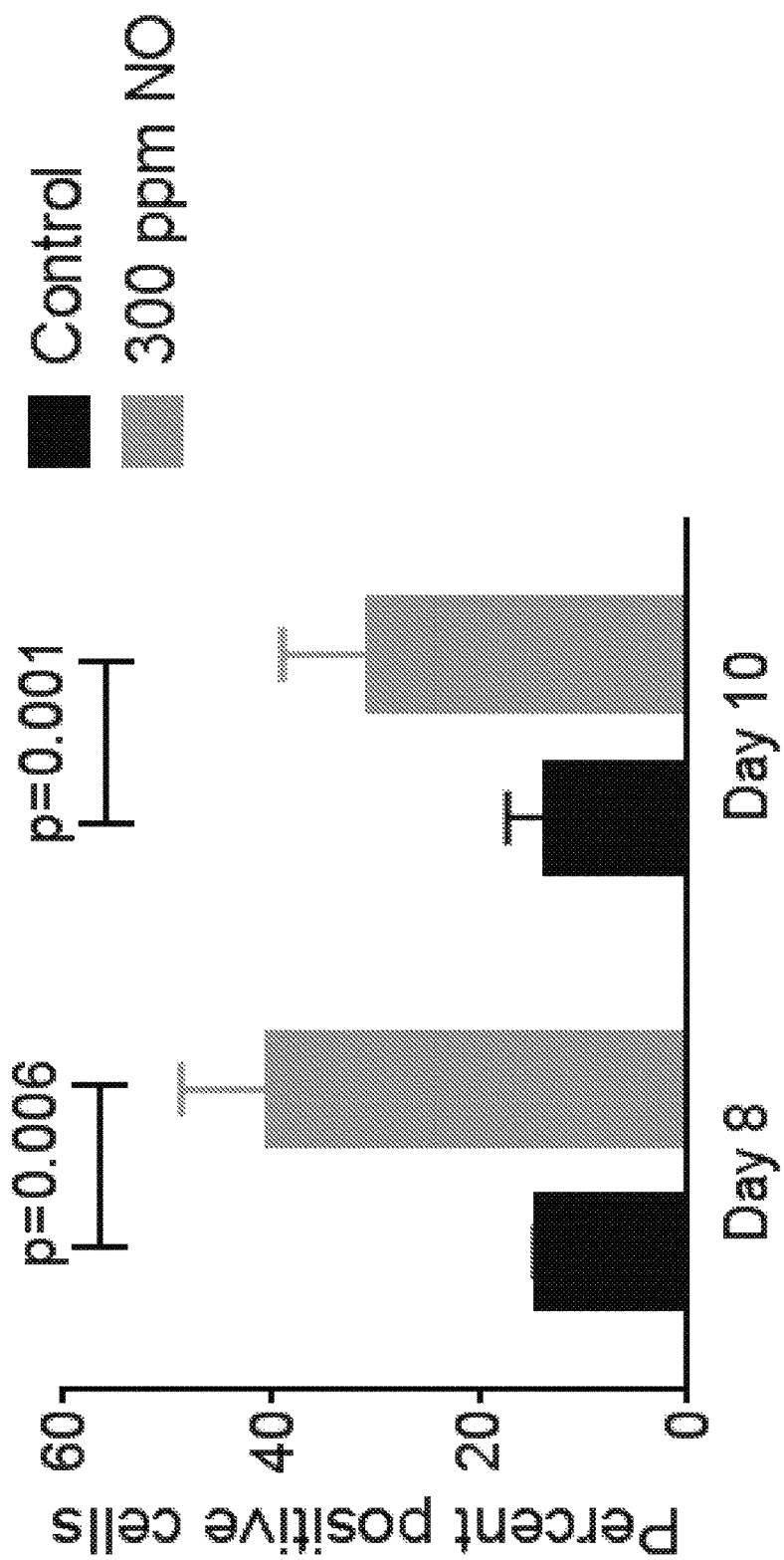
FIG. 29 shows the maximum specific binding extrapolated to very high concentrations of antibodies. Average values and standard deviation are indicated, n=3 for antibodies collected at day 8 of culture, and n=6 for antibodies collected at day 10. P values were calculated with an unpaired t test.
Figure 31:
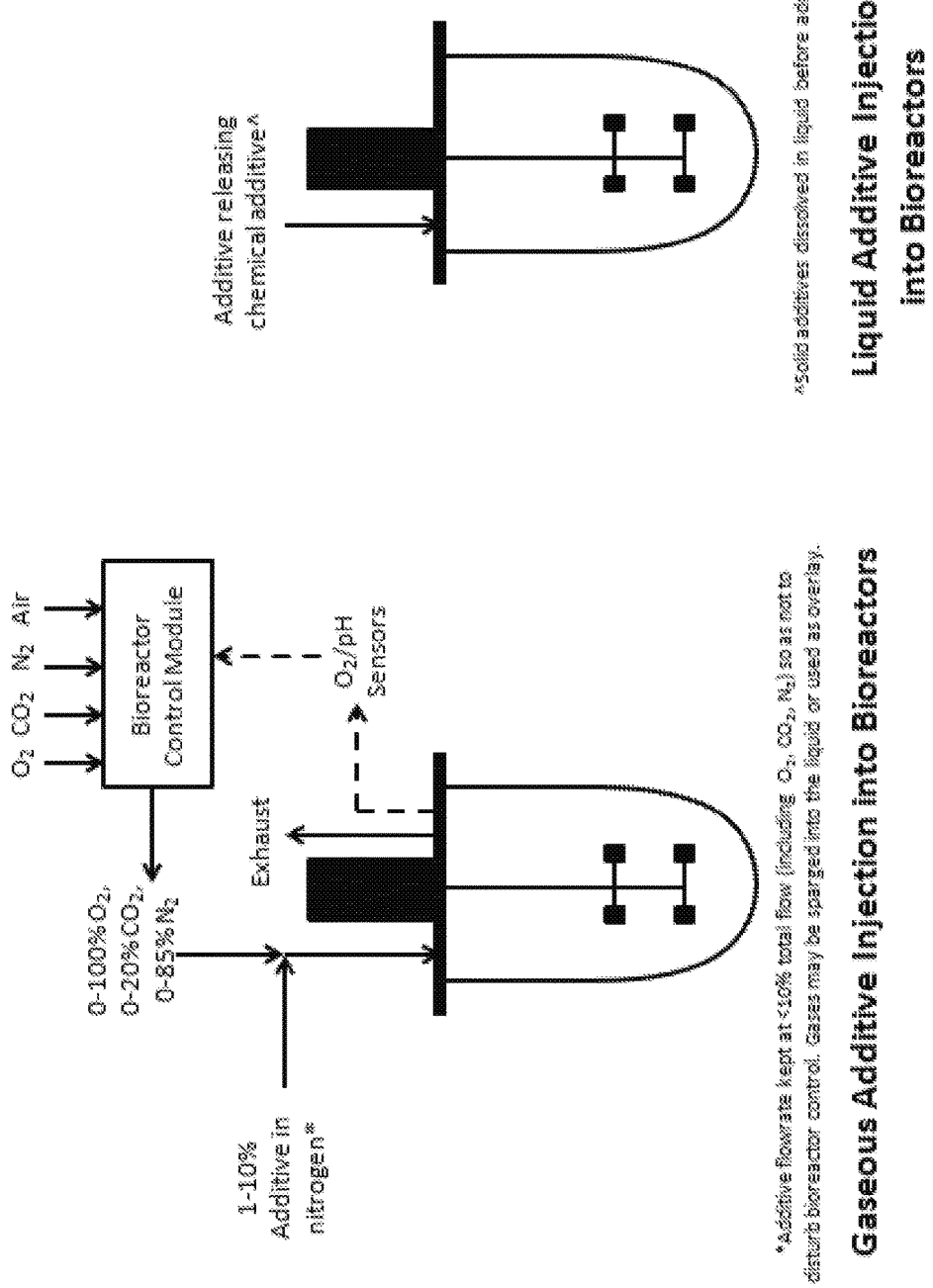
FIG. 31 shows the gas or chemical addition of the Additive to bioreactor cultures.

In order to obtain information on affinity in a more physiological setting, CHO cells expressing CD16a receptors were incubated with HBS IgGs and processed for flow cytometry (Harrison, A., Liu, Z., Makweche, S., Maskell, K., Qi, H. and Hale, G., 2012. Methods to measure the binding of therapeutic monoclonal antibodies to the human Fc receptor FcγRIII (CD16) using real time kinetic analysis and flow cytometry. Journal of pharmaceutical and biomedical analysis, 63, pp. 23-28). The number of fluorescent cells (positive cells) is proportional to the amount of IgGs bound by the Fc receptor. Antibodies obtained from bioreactors sparged with NO showed stronger binding to cells expressing CD16a receptors, compared to control antibodies (FIGS. 28 and 29). One possibility is that the observed reduction of fucosylation determines this phenotype. Afucosylated antibodies are known to have higher affinities for CD16a receptor.

Analysis of Charge Distribution

Ion exchange chromatography of antibodies is used to monitor forms resulting from asparagine deamidation, aspartic acid isomerization, disulfide interchange, peptide bond cleavage, and oxidation. IgGs were separated by ion exchange chromatography using a stationary phase containing weak positive charges (BioMAb PEEK, Agilent). Chromatography was performed using aqueous buffers at pH 5.8 or pH 7.0 with an increasing salt gradient. When compared to controls, chromatograms of IgGs derived from reactors sparged with NO appeared to have a different profile (tailing), suggesting a change in net charge on the antibody surface. Changes in net charge of IgGs were more pronounced when the ion exchange chromatography was performed at pH 5.8 (FIG. 30).

Cell Culture Formats Tested

The 3 L bioreactor batch culture format is described above. Additional testing of Nitric Oxide will be performed using a fed-batch culture. The fed batch format and parameters different from the batch cultures will be the daily addition of 150 mL of 35 g/L commercially-available Cell Boost 5 feed solution and daily adjustment of glucose and glutamine to setpoints of 4 g/L and 2.2 mM, respectively.

FED BATCH Prophetic Example:

CHO-HBS fed batch cell cultures will be performed as cell cultures were done previously with the above modifications. Nitric Oxide will induce a relative increase in titer over control cultures, analogous to the results seen with the prior cell culture experiments.

As discussed above, the results using nitric oxide in 3 L bioreactors were partially replicated in shake flasks.

INDUSTRIAL APPLICABILITY

The present invention is at least industrially applicable to the manufacture of therapeutic biologics such as monoclonal antibodies.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed. Furthermore, if there is language referring to order, such as first and second, it should be understood in an exemplary sense and not in a limiting sense. For example, it can be recognized by those skilled in the art that certain steps can be combined into a single step.

The singular forms "a", "an" and "the" include plural referents, unless the context clearly dictates otherwise.

"Comprising" in a claim is an open transitional term which means the subsequently identified claim elements are a nonexclusive listing (i.e., anything else may be additionally included and remain within the scope of "comprising"). "Comprising" as used herein may be replaced by the more limited transitional terms "consisting essentially of" and "consisting of" unless otherwise indicated herein.

"Providing" in a claim is defined to mean furnishing, supplying, making available, or preparing something. The step may be performed by any actor in the absence of express language in the claim to the contrary.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

All references identified herein are each hereby incorporated by reference into this application in their entireties, as well as for the specific information for which each is cited.

What is claimed is:

1. A method of increasing protein biomolecule production comprising the steps of:
   a) culturing a cell that produces a protein biomolecule,
   b) supplying an Additive and/or a source of the Additive to the culture medium in an amount sufficient to (i) increase a total yield of the protein biomolecule secreted into the cell culture media and/or (ii) increase a specific cellular productivity of the protein biomolecule secreted into the cell culture media,
   c) wherein the increase of step b) is measured relative to:
      culturing under a prior set of conditions established for a regulatory approval for producing the protein biomolecule and/or
      culturing under substantially the same conditions except for supplying the Additive and/or a source of the Additive,
   wherein (a) the Additive is Nitric Oxide and/or a chemical source of Nitric Oxide, (b) the cell is a eukaryotic cell, and (c) the protein biomolecule is a heterologous protein biomolecule.

2. The method of claim 1, wherein the eukaryotic cell is a Chinese hamster ovary (CHO) cell and the heterologous protein biomolecule is a monoclonal antibody.

3. The method of claim 1, wherein the Nitric Oxide is gaseous and is substituted for a portion of a volume of another gas being fed into the bioreactor.

4. The method of claim 3, wherein the other gas being fed into the bioreactor includes Oxygen gas, Nitrogen gas and/or or Carbon Dioxide gas.

5. The method of claim 1, wherein the Nitric Oxide and/or the chemical source of Nitric Oxide are added in an amount sufficient to increase a total yield of the monoclonal antibody secreted into the cell culture media.

6. The method of claim 1, wherein the Nitric Oxide and/or the chemical source of Nitric Oxide are added in an amount sufficient to increase a specific cellular productivity of the monoclonal antibody secreted into the cell culture media.

7. The method of claim 1, wherein the Nitric Oxide soluble in the cell culture medium is at a concentration of 0.1-10 nanomolar.

8. The method of claim 7, wherein the Nitric Oxide is supplied to the cell culture medium as a sparged gas at a concentration of 200-400 ppm Nitric Oxide in the sparged gas.

9. The method of claim 1, wherein the eukaryotic cell is a CHO cell and the heterologous protein biomolecule is a monoclonal antibody.

10. A cell culture medium comprising:
   a) a eukaryotic cell line that is capable of secreting a heterologous protein biomolecule, and
   b) an Additive capable of causing an increase in the amount of heterologous protein biomolecule secreted by the eukaryotic cell,
   wherein the Additive is selected from one or both of Nitric Oxide gas mixed with the cell culture medium and Nitric Oxide dissolved in the cell culture medium.

11. The cell culture medium of claim 10, wherein (a) the Additive is Nitric Oxide, (b) the eukaryotic cell line is a CHO cell line, and (c) the heterologous protein biomolecule is a monoclonal antibody.

12. The method of claim 11, wherein the Nitric Oxide soluble in the cell culture medium is within a concentration range of 0.1-10 nanomolar of Nitric Oxide.

13. A method of screening for a cell line that secretes a heterologous protein biomolecule and which is responsive to an Additive to result in an increased amount of secreted protein biomolecule, the method comprising the steps of:
   a) establishing a cell culture of the cell line that secretes the heterologous protein biomolecule,
   b) adding the Additive to the cell culture,
   c) measuring an amount of the secreted heterologous protein biomolecule protein biomolecule, and
   d) comparing the amount measured in step c) with an amount of secreted heterologous protein biomolecule representing a control condition lacking the addition of the Additive,
   wherein the Additive is selected from one or both of Nitric Oxide gas and a chemical capable of forming Nitric Oxide.

14. The method of claim 13, wherein (a) the Additive is selected from one or more of Nitric Oxide gas and a chemical capable of forming Nitric Oxide, (b) the cell line is a CHO cell line, and (c) the heterologous protein biomolecule is a monoclonal antibody.

* * * * *